United States Patent
Appledorn et al.

(10) Patent No.: US 11,481,895 B2
(45) Date of Patent: Oct. 25, 2022

(54) LIVE CELL VISUALIZATION AND ANALYSIS

(71) Applicant: Sartorius BioAnalytical Instruments, Inc., Bohemia, NY (US)

(72) Inventors: Daniel Appledorn, Ann Arbor, MI (US); Eric Endsley, Ann Arbor, MI (US); Nevine Holtz, Ann Arbor, MI (US); Brad Neagle, Ann Arbor, MI (US); David Rock, Ann Arbor, MI (US); Kirk Schroeder, Ann Arbor, MI (US)

(73) Assignee: Sartorius BioAnalytical Instruments, Inc., Bohemia, NY (US)

( * ) Notice: Subject to any disclaimer, the term of this patent is extended or adjusted under 35 U.S.C. 154(b) by 46 days.

(21) Appl. No.: 16/644,392

(22) PCT Filed: Oct. 30, 2018

(86) PCT No.: PCT/US2018/058237
§ 371 (c)(1),
(2) Date: Mar. 4, 2020

(87) PCT Pub. No.: WO2019/094230
PCT Pub. Date: May 16, 2019

(65) Prior Publication Data
US 2021/0065362 A1    Mar. 4, 2021

Related U.S. Application Data

(60) Provisional application No. 62/584,388, filed on Nov. 10, 2017.

(51) Int. Cl.
*G06K 9/00* (2022.01)
*G06T 7/00* (2017.01)
(Continued)

(52) U.S. Cl.
CPC ............ *G06T 7/0012* (2013.01); *G06T 7/254* (2017.01); *G06V 20/698* (2022.01); *G16B 45/00* (2019.02);
(Continued)

(58) Field of Classification Search
None
See application file for complete search history.

(56) References Cited

U.S. PATENT DOCUMENTS

| 10,043,054 B2 | 8/2018 | Remiszewski |
| 2012/0315660 A1 | 12/2012 | Schroeder et al. |
| 2015/0050684 A1 | 2/2015 | Seo et al. |

FOREIGN PATENT DOCUMENTS

CA    2591959 A1    6/2006

OTHER PUBLICATIONS

King et al., "A high-thoughput microfluidic real-time gene expression living cell array" (Year: 2006).*

(Continued)

*Primary Examiner* — Soo Jin Park
(74) *Attorney, Agent, or Firm* — McDonnell Boehnen Hulbert & Berghoff LLP

(57) ABSTRACT

Systems and methods are provided for automatically imaging and analyzing cell samples in an incubator. An actuated microscope operates to generate images of samples within wells of a sample container across days, weeks, or months. A plurality of images is generated for each scan of a particular well, and the images within such a scan are used to image and analysis metabolically active cells in the well. Tins analysis includes generating a "range image" by subtracting the minimum intensity value, across the scan, for each pixel from the maximum intensity value. This range image thus emphasizes cells or portions of cells that exhibit changes in activity over a scan period (e.g., neurons, myo- (Continued)

cytes, cardiomyocytes) while de-emphasizing regions that exhibit consistently high intensities when images (e.g., regions exhibiting a great deal of autofluorescence unrelated to cell activity).

21 Claims, 43 Drawing Sheets

(51) Int. Cl.
*G06T 7/254* (2017.01)
*G16B 45/00* (2019.01)
*G06V 20/69* (2022.01)

(52) U.S. Cl.
CPC .............. *G06T 2207/10056* (2013.01); *G06T 2207/10064* (2013.01); *G06T 2207/30024* (2013.01); *G06T 2207/30072* (2013.01)

(56) References Cited

OTHER PUBLICATIONS

Extended European Search Report for corresponding European application No. 18875690.2, dated Dec. 13, 2021.
The International Search Report (ISR) with Written Opinion for PCT/US2018/058237 dated Feb. 27, 2019, pp. 1-12.
Mellen, Nicholas M et al. Semi-automated region of interest generation for the analysis of optically recorded neuronal activity' Neuroimage (2009) vol. 47., pp. 1331-1340.
Seynhaeve, Ann L.B. "Using In Vitro Live-cell Imaging to Explore Chemotherapeutics Delivered by Lipid-based Nanoparticles" Journal of Visualized Experiments (2017) vol. 129(e55405), pp. 1-12.
O'Clair, Lindy et al. "Visualize Chemotaxis in Real Time" Genetic Engineering & Biotechnology News (2017) vol. 37(7), pp. 12-13.

* cited by examiner

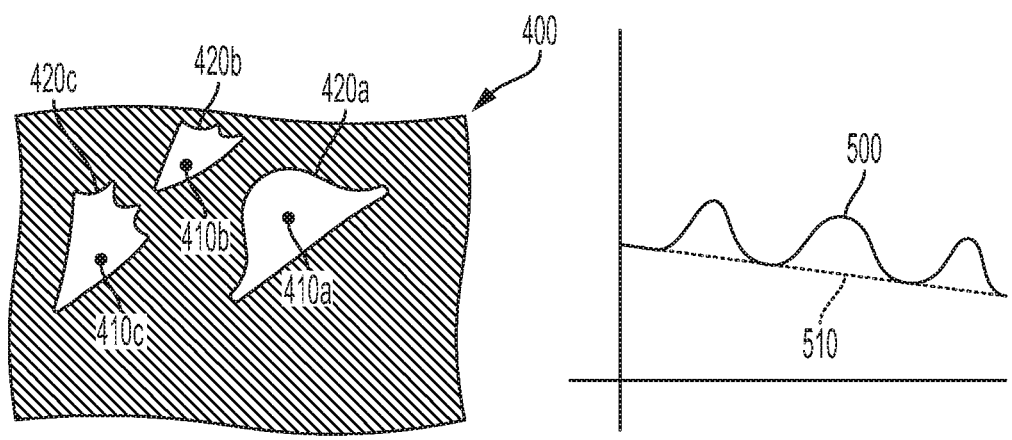
FIGURE 4
FIGURE 5A
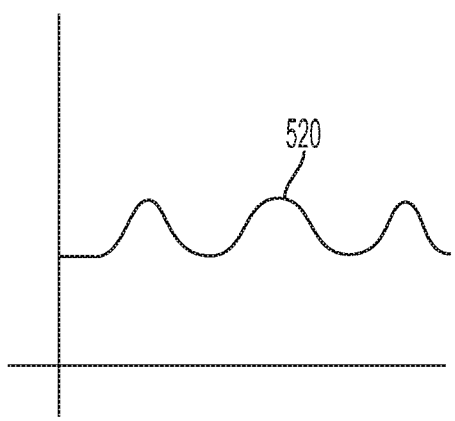
FIGURE 5B
FIGURE 5C

Live-cell Analysis System

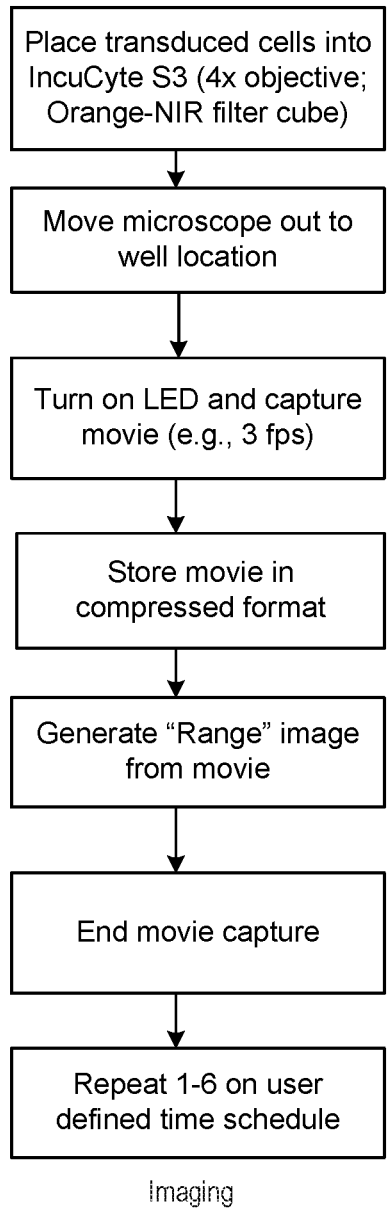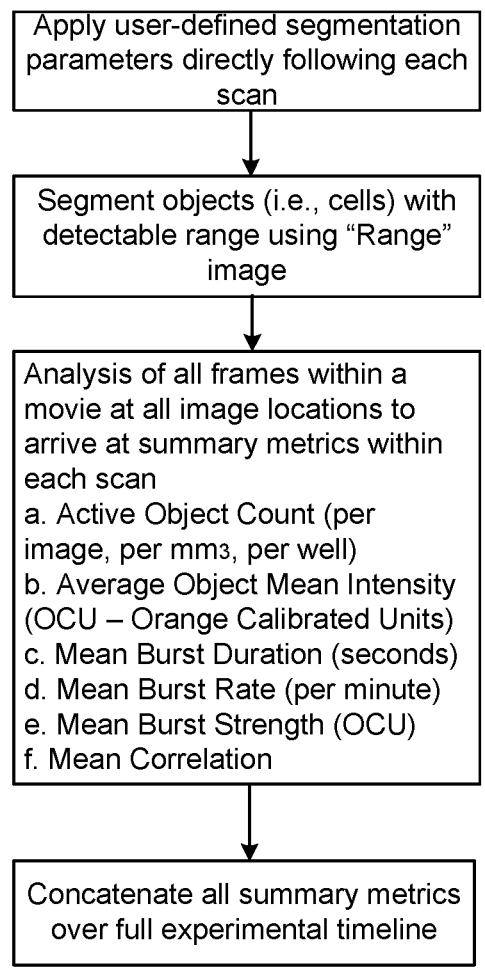
FIGURE 10
FIGURE 11

Automated Neuronal Activity Analysis & Metrics

Visualize full set of data at every time point Fluorescent image represents activity range over complete 3' video capture. Quickly see differences in active objects. Built-in analytical tools facilitate data analysis for the typical biologist. Unsegmented range image (left) and segmented range image (right).

Automated Neuronal Activity Analysis & Metrics

User interface designed to visualize full set of data at every time point. Fluorescent image represents activity "Range" over complete 3-minute video capture. Quickly see differences in active objects.

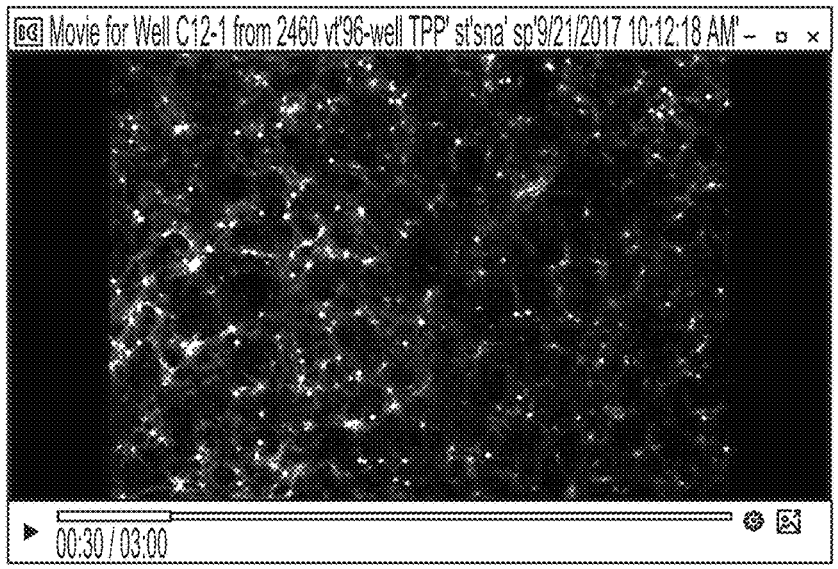

Movie viewing and export tools
Movie viewing and movie export tools are integrated within the user interface for simple, qualitative data viewing. Phase contrast images are also provided for a qualitative check on cell morphology and culture health (image not shown).

FIGURE 13C

- Active object count (per image)
  - The number of objects that burst at least once over the 3 minute scan
- Object Mean Intensity (OCU)
  - The mean intensity of all objects over the total scan time
- Mean Burst Strength (OCU)
  - Area under each burst divided by the duration of that burst over the total scan time
- Mean Burst Rate (bursts/min)
  - The number of bursts over the total scan time
- Mean Correlation (low=0, high=1)
  - The mean correlation of each pair of objects within the image (connectivity)

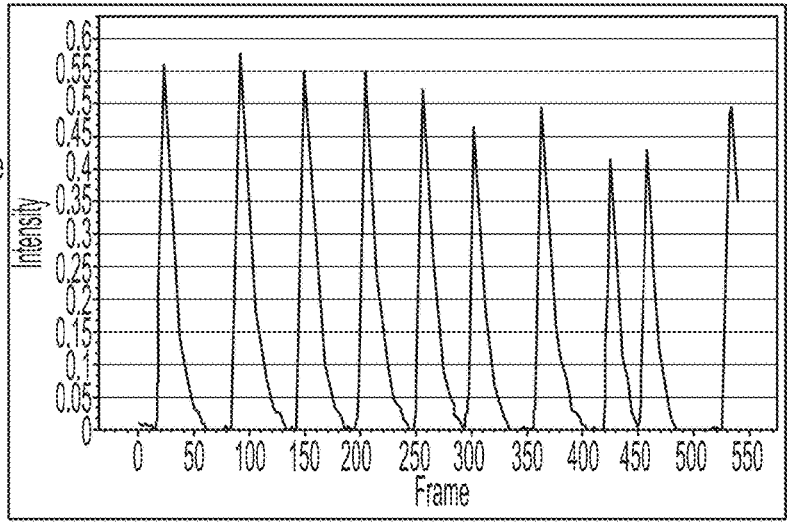

Automated Neuronal Activity Analysis & Metrics
A high-level description of metrics provided at each scheduled scan. Built in analytical tools facilitate data analysis for the typical biologist.

FIGURE 13D

Automated Neuronal Activity Analysis & Metrics
Quickly see differences in traces of activity for single objects (cells).

Automated Neuronal Activity Analysis & Metrics
Quickly see differences in traces of activity for all cells within an image

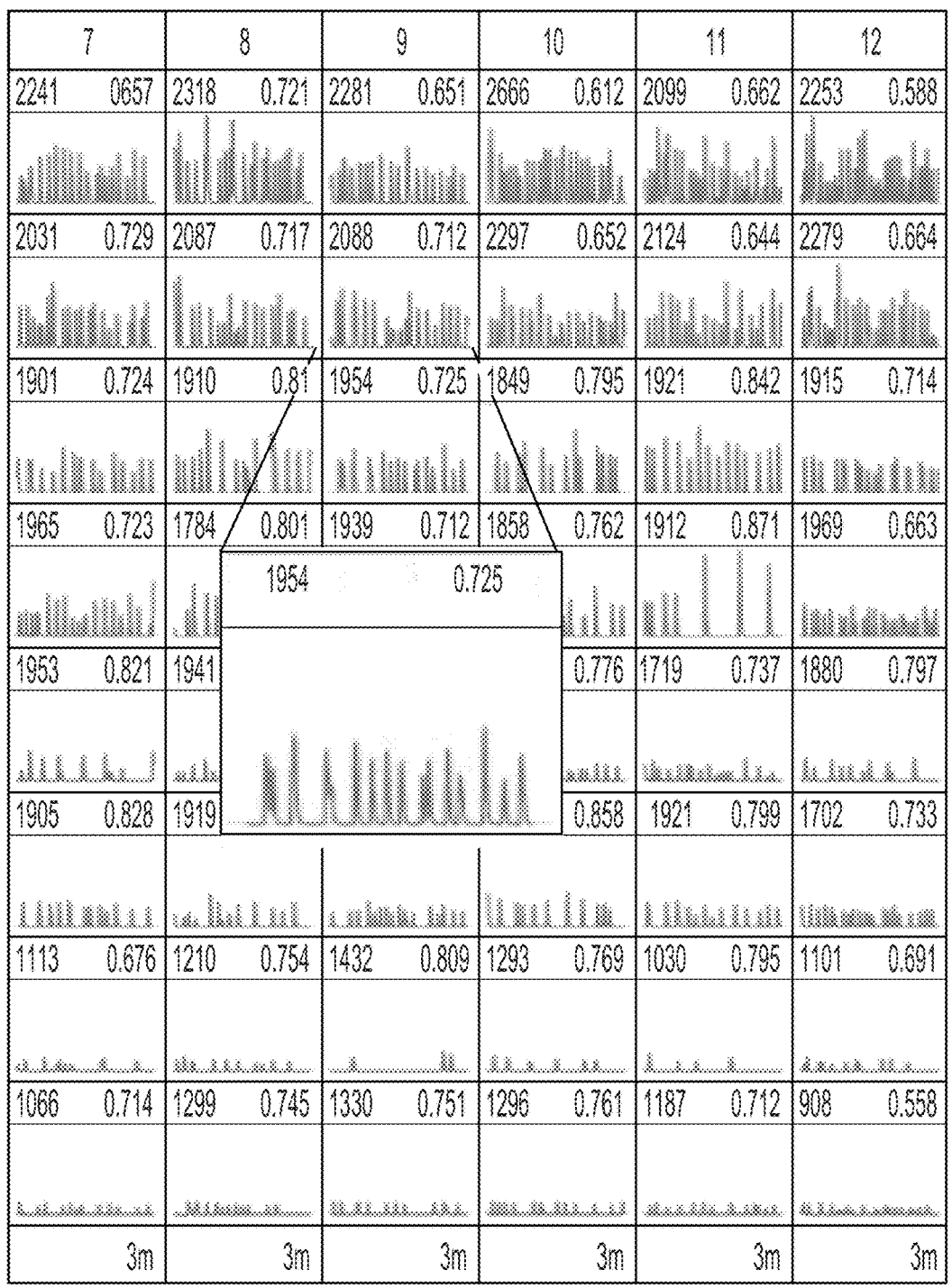

After each scan, the user can plot the average intensity of all objects in this 96-well microplate representation of the data. The number of active objects for which these data are derived can be found in the top left corner of each well location while the average correlation (a measure of connectivity/synchronicity) can be found in the top right corner. The x-axis in each well location is time (total 3 min scan) while the y-axis describes the average flourescence intensity of all measured objects within the well

FIGURE 13I

Pharmacological effects of Picrotoxin and Tetrodotoxin on E18 rat forebrain neurons Pre-treatment scan

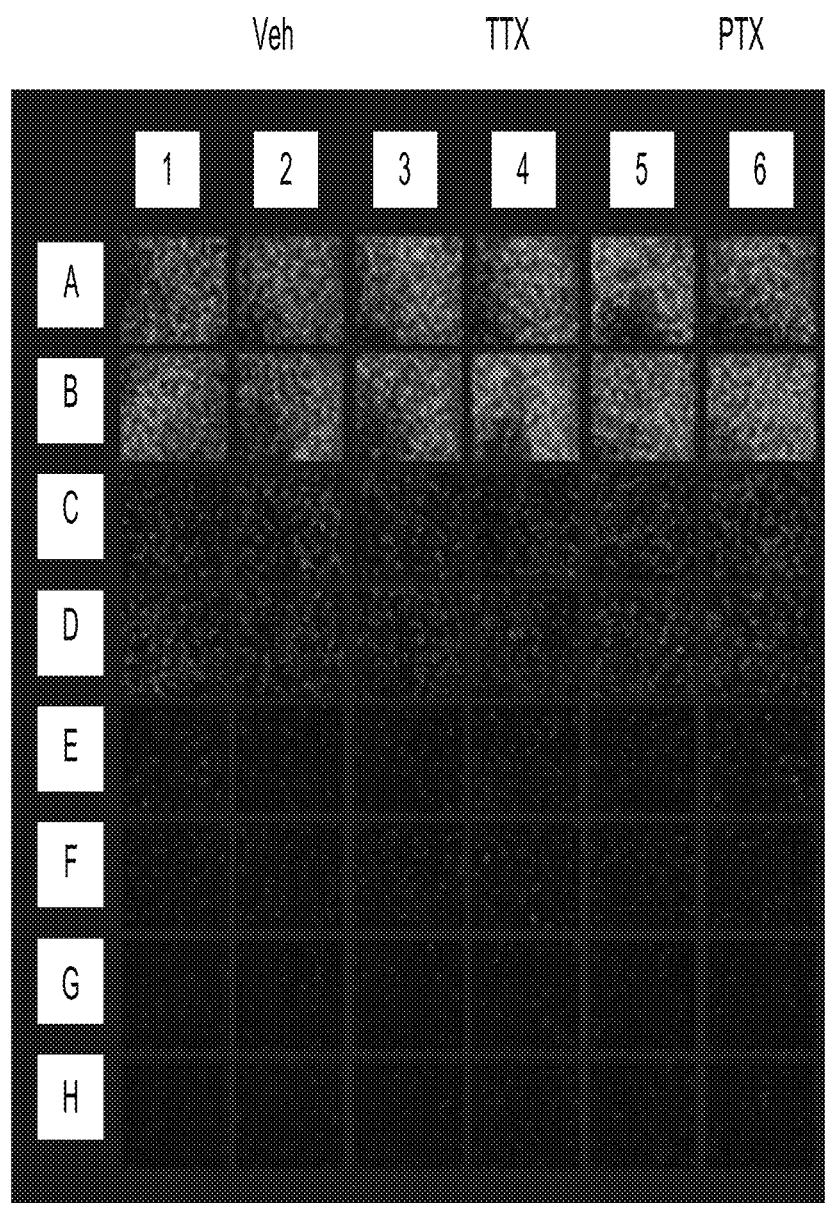

Endpoint pharmacology with tetrodotoxin (TTX, 1 μm) or picrotoxin (PTX, 100 μM). PTX treatment increases rate of bursting and correlation (connectivity). TTX treatment significantly decreases all measured metrics, indicating the activity measured is synaptically driven

FIGURE 13J

|  | Veh | | TTX | | PTX | |
|---|---|---|---|---|---|---|
| | 1 | 2 | 3 | 4 | 5 | 6 |
| 9.71 A 0 | 1878 0.677 | 1772 0.63 | 1726 0.727 | 2004 0.717 | 1801 0.789 | 1904 0.672 |
| 9.71 B 0 | 1950 0.741 | 1661 0.735 | 1520 0.774 | 1399 0.788 | 1822 0.814 | 1604 0.862 |
| 9.71 C 0 | 1642 0.444 | 1567 0.545 | 1633 0.536 | 1647 0.482 | 1534 0.479 | 1556 0.599 |
| 9.71 D 0 | 1622 0.493 | 1620 0.49 | 1647 0.468 | 1619 0.524 | 1595 0.561 | 1555 0.516 |
| 9.71 E 0 | 1321 0.446 | 1477 0.439 | 1274 0.431 | 1598 0.576 | 1470 0.458 | 1605 0.606 |
| 9.71 F 0 | 1289 0.554 | 1409 0.435 | 1286 0.381 | 1456 0.461 | 1581 0.603 | 1388 0.462 |
| 9.71 G 0 | 890 0.404 | 998 0.519 | 1117 0.501 | 1066 0.554 | 1148 0.487 | 1142 0.516 |
| 9.71 H 0 | 958 0.539 | 1140 0.561 | 1061 0.465 | 1346 0.519 | 1157 0.522 | 1000 0.438 |
| | 3m | 3m | 3m | 3m | 3m | 3m |

FIGURE 13K

|     | Veh | | TTX | | PTX | |
| --- | --- | --- | --- | --- | --- | --- |
|     | 1 | 2 | 3 | 4 | 5 | 6 |
| 8.24 A 0 | 1777  0.704 | 1671  0.804 | 95  0.04 | 79  0.053 | 2049  0.901 | 2116  0.904 |
| 8.24 B 0 | 1527  0.812 | 1.625  0.801 | 105  0.059 | 132  0.059 | 2274  0.859 | 2088  0.887 |
| 8.24 C 0 | 1306  0.508 | 1590  0.684 | 43  0.038 | 27  0.028 | 1820  0.935 | 1878  0.933 |
| 8.24 D 0 | 1489  0.481 | 1580  0.504 | 31  0.05 | 46  0.063 | 1732  0.933 | 1524  0.923 |
| 8.24 E 0 | 1190  0.372 | 1449  0.391 | 10  0.044 | 10  0.057 | 1686  0.911 | 1828  0.931 |
| 8.24 F 0 | 1271  0.503 | 1487  0.403 | 14  0.035 | 18  0.168 | 1605  0.896 | 1724  0.918 |
| 8.24 G 0 | 900  0.383 | 1005  0.46 | 6  0.039 | 4  0.04 | 1318  0.938 | 1430  0.933 |
| 8.24 H 0 | 912  0.469 | 047  0.504 | 1  0 | 6  0.092 | 1394  0.946 | 920  0.872 |
|     | 3m | 3m | 3m | 3m | 3m | 3m |

FIGURE 13L

Experimental design for iCell GlutaNeurons

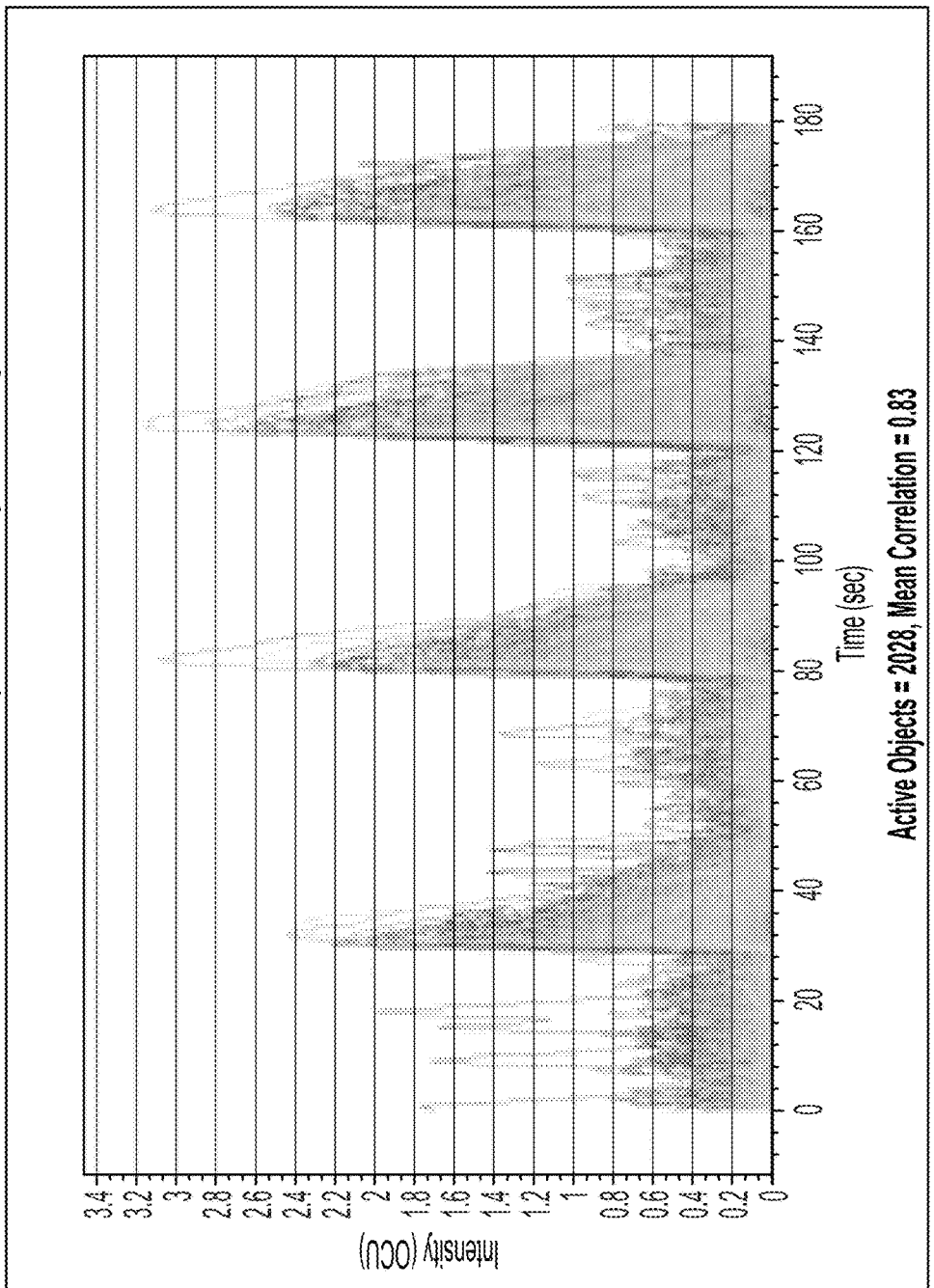

FIG. 16H

Example traces of all active objects/well throughout the experiment of Day 3 GECI infection. Mean burst rate kinetic graph included to highlight activity (trace) differences over time. Notice the difference in correlated activity as well (uncorrelated at early time points, more correlated at later time points). The changes in burst rate were not expected. Clearly this has a big impact on when the experiment would be performed.

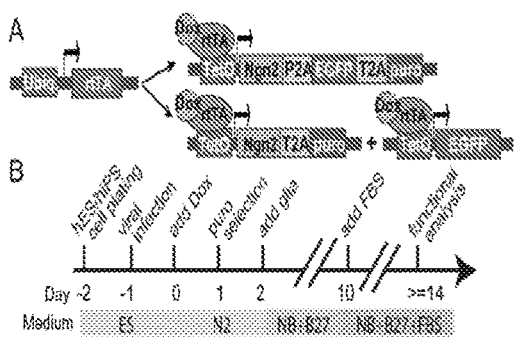

- Tested cells stably expressing GECI
- Tested several densities and viral MOIs of cells transduced with the GECI
- Cells are plated, allowed to differentiate for 7 days, then transduced with GECI
- All cultured in the presence of rAstrocytes at 15K per well
- Coating: Matrigel
- 2 types of media: BrainPhys and 3N + SM1 supplement
  - Grown in presence or absence of Growth Factor (GF)
- 50% media exchange (2x weekly)
- Scanned for activity every 24 hours Activity measurements were also made in iNeurons

FIGURE 18A

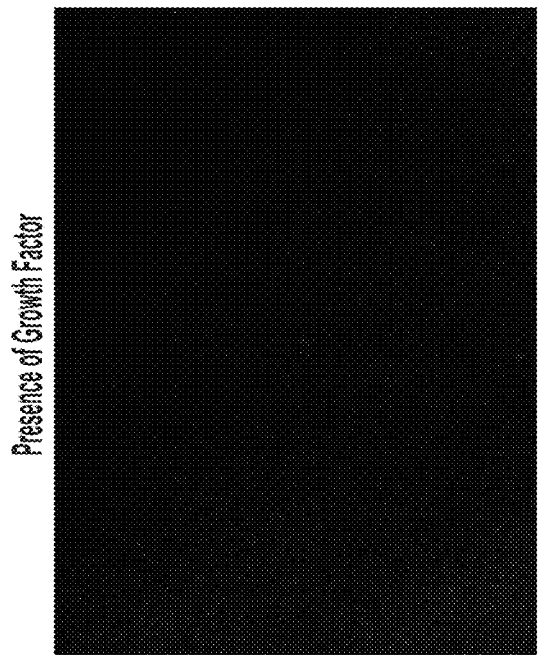
Presence of Growth Factor
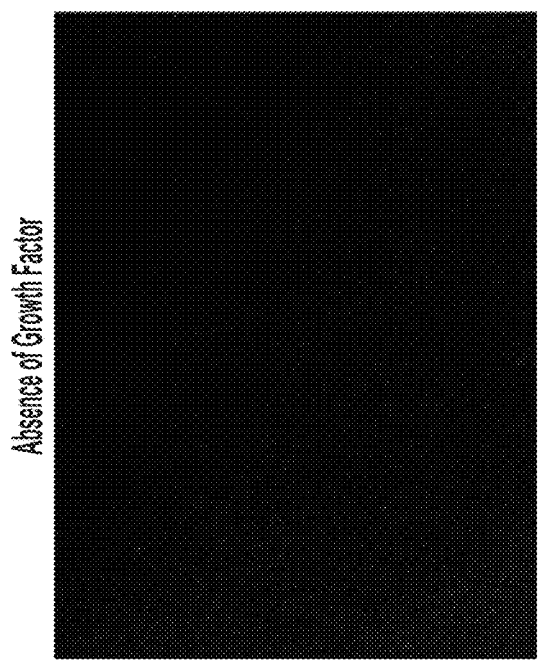
Absence of Growth Factor
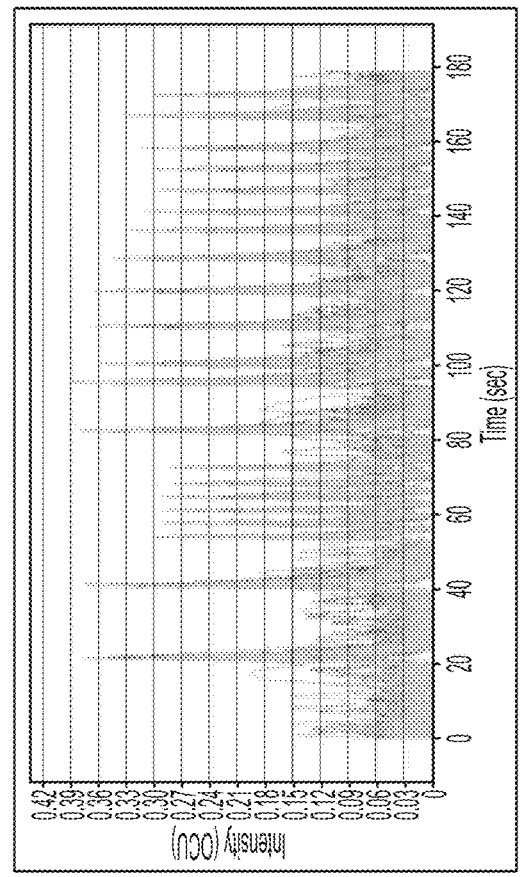
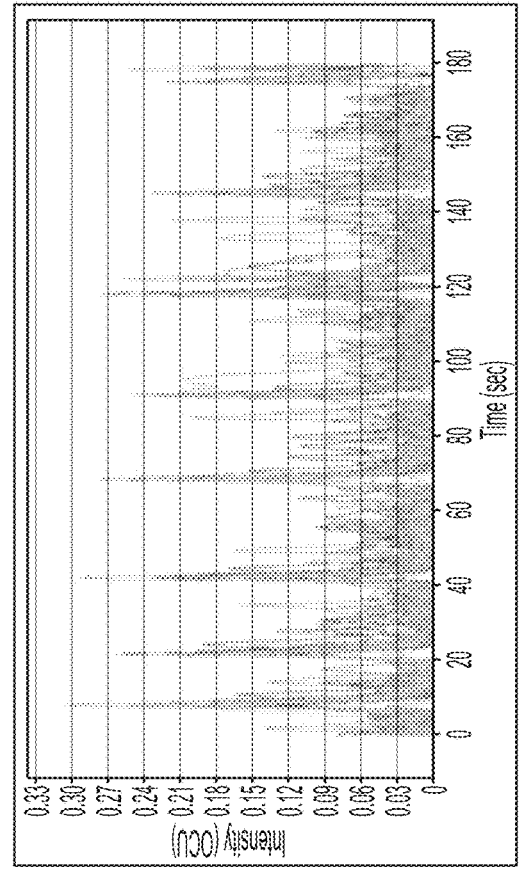
Movies and traces of iNeurons
FIGURE 18C

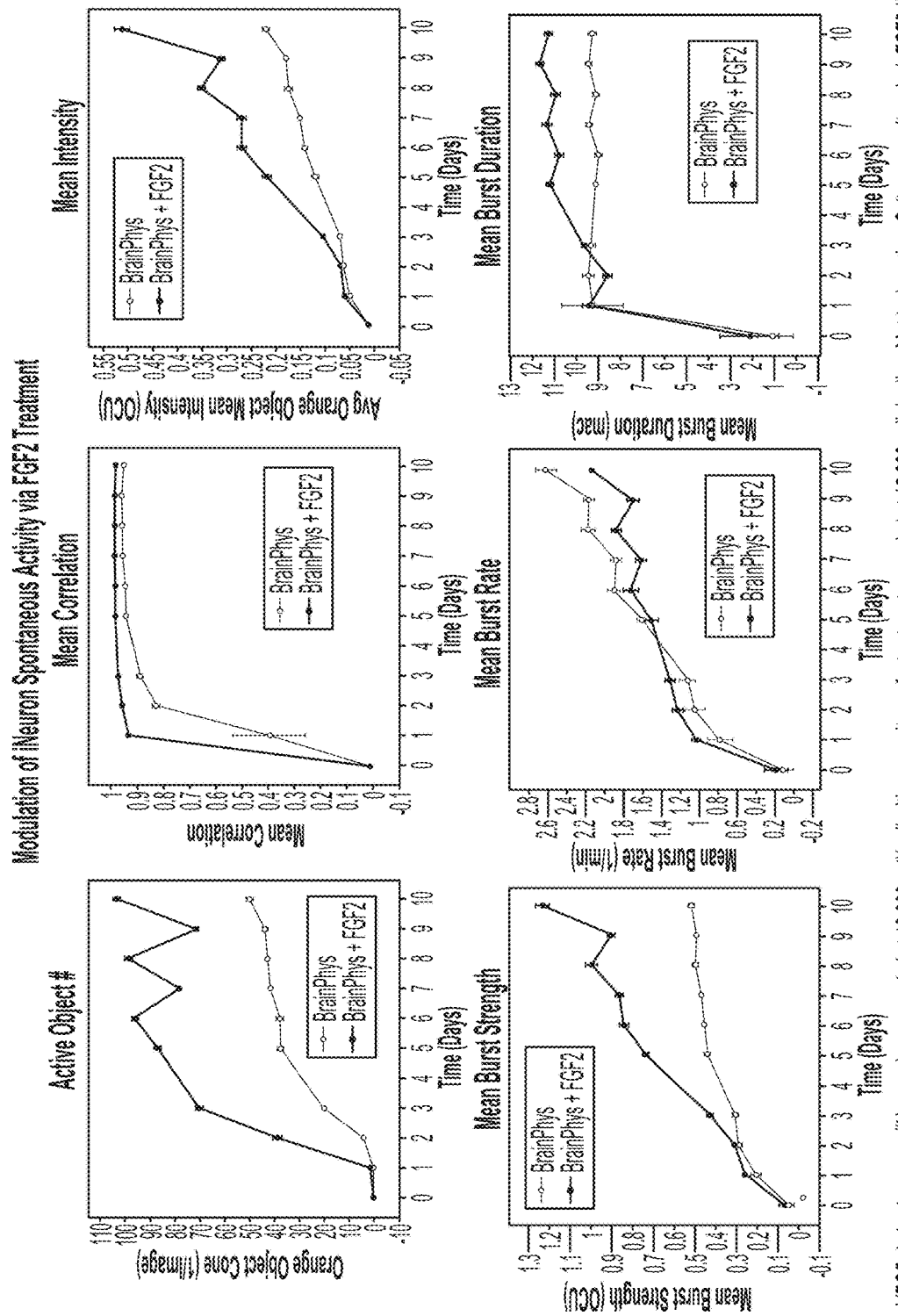

FIGURE 18E

Induced iPSC-derived neurons (iNeurons) were seeded at 10,000 cell/well with a co-culture of rat astrocytes seeded at 15,000 cells/well on Matrigel coating. Cells were cultured +/- FGF2 (20 ng/ml). iNeurons were infected with GECI reagent at Day 21, and automated metrics of spontaneous activity were quantified for 10 days after infection. n≥3. FGF2 treatment increased active object #, mean burst intensity, mean burst strength and mean burst duration. Mean correlation increased with faster kinetics following FGF2 treatment, while mean burst rate was decreased.

Summary - iNeurons

> Significant activity not detected until day 14 (or beyond)
> No activity detected in 3N medium; BrainPhys was required
> Presence of "Growth Factor" had a significant and profound effect on kinetics of network maturation as well as all activity metrics
> Presence of "Growth Factor" had less of an effect on connectivity, i.e. once the cells became active, they were mostly correlated/synchronous
> Presence of complex neuronal morphology does not predict activity

| All | 1 | 2 | 3 | 4 | 5 | 6 | 7 | 8 | 9 | 10 | 11 | 12 |
|---|---|---|---|---|---|---|---|---|---|---|---|---|
| A | \multicolumn{6}{l|}{fForebrain Neurons (1) 40K/well; rAstrocytes (2) 15K/well; DIV2 Infection; BrainPhys Media; 80 µL GECI} | | | | | | | |
| B | | | | | | | | | | | | |
| C | \multicolumn{6}{l|}{fForebrain Neurons (1) 20K/well; rAstrocytes (2) 15K/well; DIV2 Infection; BrainPhys Media; 40 µL GECI} | | | | | | | |
| D | | | | | | | | | | | | |
| E | \multicolumn{6}{l|}{fForebrain Neurons (1) 10K/well; rAstrocytes (2) 15K/well; DIV2 Infection; BrainPhys Media; 20 µL GECI} | | | | | | | |
| F | | | | | | | | | | | | |
| G | \multicolumn{6}{l|}{fForebrain Neurons (1) 5K/well; rAstrocytes (2) 15K/well; DIV2 Infection; BrainPhys Media; 10 µL GECI} | | | | | | | |
| H | | | | | | | | | | | | |

Columns 7-12 (hatched):
- Rows A-B: fForebrain Neurons (1) 40K/well; rAstrocytes (2) 15K/well; DIV2 Infection; Neurobasal Media; 80 µL GECI
- Rows C-D: fForebrain Neurons (1) 20K/well; rAstrocytes (2) 15K/well; DIV2 Infection; Neurobasal Media; 40 µL GECI
- Rows E-F: fForebrain Neurons (1) 10K/well; rAstrocytes (2) 15K/well; DIV2 Infection; Neurobasal Media; 20 µL GECI
- Rows G-H: fForebrain Neurons (1) 5K/well; rAstrocytes (2) 15K/well; DIV2 Infection; Neurobasal Media; 10 µL GECI Cell # (decreasing from A to H)

Density optimization of E18 rat forebrain neurons

- Tested 4 densities
  - 40K per well
  - 20K per well
  - 10K per well
  - 5K per well
- All cultured in the presence of rAstrocytes at 15K per well
- Coating: PDL
- 2 types of media: BrainPhys (Blue) and Neurobasal (Red) + SM1 supplement
- 50% media exchange (2x weekly)
- Scanned for activity every 24 hours The effect of growth media (neurobasal vs. BrainPhys) on activity of E18 Rat Forebrain neurons in co-culture. Very minor effects on number of active objects, mean burst strength and correlation were observed. More significant effects on burst duration, burst rate and mean intensity were observed over the course of this 15-day assay.

Multiple types of neurons

| Cells | Type | Setup | Vendor | Differentiation | Media Pref | D or 2D |
|---|---|---|---|---|---|---|
| Rat E18 Forebrain | Primary | Co-culture | Thermo/Global Stem | NA | BrainPhys or NB | 7 days |
| iCell GlutaNeurons | iPSC | Mono and Co | CDI | Unknown | BrainPhys | 7 days |
| iCell GABANeurons | iPSC | Mono and Co | CDI | Unknown | BrainPhys | ?? |
| iCell DopaNeurons | iPSC | Co-culture | CDI | Unknown | BrainPhys | 12-15 days |
| MyCell DopaNeurons (A53T) | iPSC | Co-culture | CDI | Unknown | BrainPhys | 12-15 days |
| Peri.4U | iPSC | Co-culture | Ncardia | Unknown | Ncardia | >30 days ?? |
| CNS.4U | iPSC | Co-culture | Ncardia | Unknown | Ncardia | 32-34 days |
| iNeurons | iPSC | Co-culture | Academic | Neurogenin2 | BrainPhys | 16-20 days |

FIGURE 22

LIVE CELL VISUALIZATION AND ANALYSIS

CROSS-REFERENCE TO RELATED APPLICATION

This application is a U.S. national phase of International Application No. PCT/US2018/058237, filed on Oct. 30, 2018, which claims priority to U.S. Provisional Application No. 62/584,388, filed Nov. 10, 2017, both of which are incorporated by reference herein in their entirety.

BACKGROUND

Cells (e.g., cultured cells, explanted tissue samples) can be incubated in a variety of media and exposed to a variety of conditions (e.g., temperature, dissolved gas levels, radiation, humidity, added substances, electrical or magnetic fields, viruses, microorganisms) in order to assess the response of the cells to the applied conditions. The response of the cells to the applied conditions can be measured in order to assess the efficacy of a drug or treatment, to assess the toxicity of a substance (e.g., of an experimental drug or treatment), to investigate the effect of a genetic modification of the cells, to investigate the metabolomics, structure, or other properties of the cells and/or tissue formed therefrom, or to determine some other information. This assessment can include removing the sample from the incubator and imaging it (for example, using a fluorescence microscope or some other imaging apparatus). This imaging can include the addition of contrast agents or chemical reagents the may result in destruction of the sample. However, this method perturbs the sample being imaged, thus requiring multiple sets of samples to be incubated, for respective different time durations, in order to assess the response of the population of samples over time.

SUMMARY

An aspect of the present disclosure relates to a method including: (i) capturing a movie of a cell culture vessel; and (ii) generating a static range image from the movie, wherein the range image is composed of pixels representing the minimum fluorescence intensity subtracted from the maximum fluorescence intensity at each pixel location over a complete scan period.

Another aspect of the present disclosure relates to a method of identifying biologically active cells during one or more periods of time. The method includes, for each of the one or more periods of time: (i) generating a plurality of fluorescence activity images of a sample contained within a sample container, wherein the sample includes biologically active cells, and wherein each image of the plurality of fluorescence activity images includes a respective plurality of pixel values, each pixel value corresponding to a respective pixel location within an image frame; (ii) generating a fluorescence range image from the plurality of fluorescence activity images by determining a plurality of pixel values for the fluorescence range image, wherein determining a given pixel value for the fluorescence range image includes determining a range of a set of pixel values, from each of the plurality of fluorescence activity images, that have pixel locations corresponding to a pixel location of the given pixel value within the image frame; (iii) based on the fluorescence range image, determining a location, relative to the image frame, of one or more active objects within the sample container during a corresponding period of time, wherein each of the one or more active objects is a portion of at least one respective biologically active cell present within the sample during the corresponding period of time; and (iv) for each active object of the one or more active objects within the sample container during the corresponding period of time, determining a respective time-varying activity level of each of the one or more active objects across the corresponding period of time. Determining a respective time-varying activity level of each of the one or more active objects across the corresponding period of time can include determining each time-varying activity level based on a set of pixel values, from each of the plurality of fluorescence activity images, that have pixel locations proximate to the determined location of a corresponding active object.

Yet another aspect of the present disclosure relates to a method of identifying biologically active cells during one or more periods of time. The method includes, for each of the one or more periods of time: (i) generating a plurality of fluorescence activity images of a sample contained within a sample container, wherein the sample includes biologically active cells, and wherein each image of the plurality of fluorescence activity images includes a respective plurality of pixel values, each pixel value corresponding to a respective pixel location within an image frame; (ii) determining a location, relative to the image frame, of one or more active objects within the sample container during a corresponding period of time, wherein each of the one or more active objects is a portion of at least one respective biologically active cell present within the sample during the corresponding period of time; (iii) for each of the one or more active objects within the sample container during the corresponding period of time, determining a respective time-varying activity level across the corresponding period of time; and (iv) based on the time-varying activity levels determined for the one or more active objects, selecting a subset of active objects from the one or more active objects by determining that the time-varying activity level determined for the particular active object exhibits at least one burst. Determining a respective time-varying activity level across the corresponding period of time can include determining the respective time-varying activity level based on a respective set of pixel values, from each of the plurality of fluorescence activity images, that have pixel locations proximate to the respective determined location of the one or more active objects.

Yet another aspect of the present disclosure relates to a non-transitory computer-readable medium that is configured to store at least computer-readable instructions that, when executed by one or more processors of a computing device, cause the computing device to perform computer operations carrying out one or more of the methods described herein.

Yet another aspect of the present disclosure relates to a system including: (i) one or more processors; and (ii) a non-transitory computer-readable medium that is configured to store at least computer-readable instructions that, when executed by the one or more processors, cause the system to perform one or more of the methods described herein.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

BRIEF DESCRIPTION OF THE FIGURES

FIG. 4 depicts a segmentation of the "range image" of FIG. 3.

FIG. 5A depicts an example time-varying activity trace determined for a cell or a portion of a cell.

FIG. 5B depicts an example time-varying activity trace determined for a cell or a portion of a cell.

FIG. 5C depicts an example time-varying photobleaching curve determined for a series of images of a sample.

FIG. 10 is a flowchart of an example method.

FIG. 11 is a flowchart of an example method.

FIG. 13C depicts example experimental results obtained using the systems and methods depicted herein.

FIG. 13D depicts example experimental results obtained using the systems and methods depicted herein.

FIG. 13I depicts example experimental results obtained using the systems and methods depicted herein.

FIG. 13J depicts example experimental results obtained using the systems and methods depicted herein.

FIG. 13K depicts example experimental results obtained using the systems and methods depicted herein.

FIG. 13L depicts example experimental results obtained using the systems and methods depicted herein.

FIG. 16H depicts example experimental results obtained using the systems and methods depicted herein.

FIG. 18A depicts example experimental results obtained using the systems and methods depicted herein.

FIG. 18C depicts example experimental results obtained using the systems and methods depicted herein.

FIG. 18E depicts example experimental results obtained using the systems and methods depicted herein.

FIG. 18F depicts example experimental results obtained using the systems and methods depicted herein.

FIG. 19 depicts example experimental results obtained using the systems and methods depicted herein.

FIG. 22 depicts example experimental results obtained using the systems and methods depicted herein.

Figure 1:
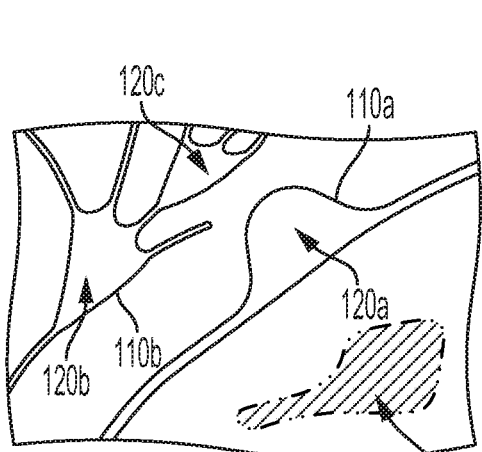
FIG. 1 depicts an example sample containing cells.
Figure 2A:
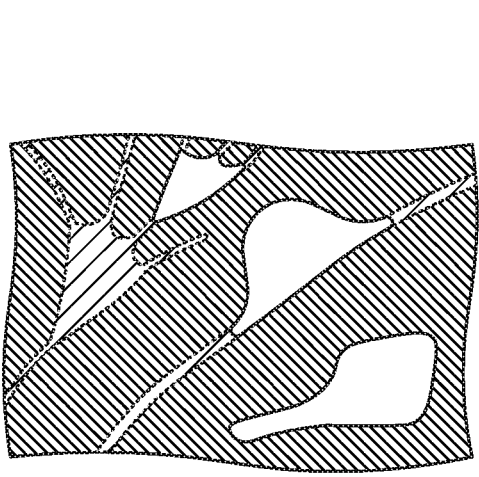
FIG. 2A depicts an image, taken at a first point in time, of the sample of FIG. 1.
Figure 2B:
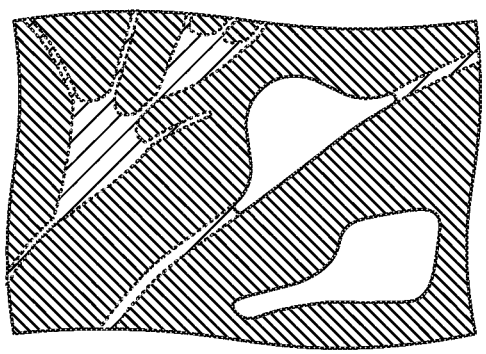
FIG. 2B depicts an image, taken at a second point in time, of the sample of FIG. 1.
Figure 2C:
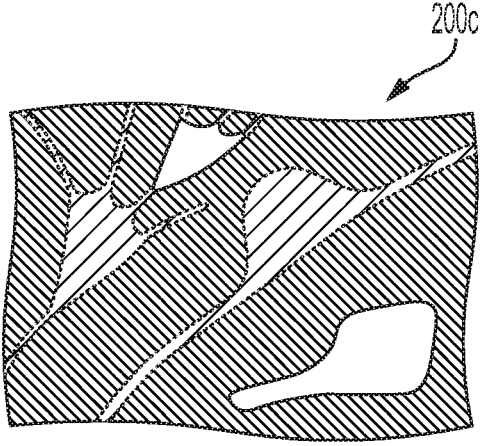
FIG. 2C depicts an image, taken at a third point in time, of the sample of FIG. 1.
Figure 2D:
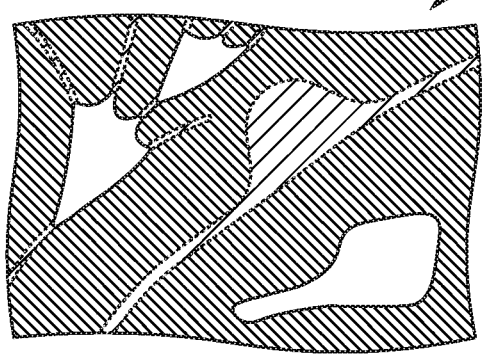
FIG. 2D depicts an image, taken at a fourth point in time, of the sample of FIG. 1.
Figure 3:
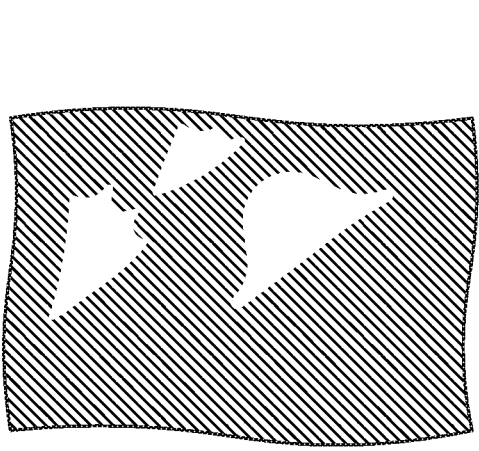
FIG. 3 depicts a "range image" generated from the images of FIGS. 2A-D.

The patent or application file contains at least one drawing executed in color. Copies of this patent or patent application publication with color drawing(s) will be provided by the Office upon request and payment of the necessary fee.

DETAILED DESCRIPTION

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. Overview

It is desirable in a variety of applications to measure and analyze the behavior of tissue and/or cell samples over time (e.g., hours, days, weeks, or months or any other suitable periods of time). Such detection and analysis can facilitate the assessment of a variety of therapeutic treatments, environmental conditions, genetic modifications, communicable diseases, or other specified conditions over time in order to assess the efficacy of a treatment, to determine the toxicity of a substance, or to determine some other information of interest. This detection and analysis can include imaging the cell and/or tissue samples. Such imaging can include generating, for a plurality of different periods of time (for example, hourly, daily, weekly, twice-daily, or other suitable sets of periods of time) movies or other sequences of images depicting the structure and/or activity of the samples across each period of time. A "movie" can include all of the images taken of a sample during a particular period of time, or may include a subset of such images.

Such image sequences could provide information about the pattern or structure of the activity of the cells in a sample. A degree of connectivity between a pair of cells, portions of cells, or other "active objects" in a sample can be determined as a correlation or coherence between time-varying activity levels determined for the pair of active objects, the presence, magnitude, width, or some other measure of a peak or other feature of a measured probability function that describes a relationship between the activity of pairs of cells, or some other metric of the degree of similarity and/or causality between the measured activity levels, over time, of pairs of active objects in a sample. A degree of connectivity of a population of active objects in a sample could be determined as a mean or other summary metric of such pairwise measures. A pattern of connectivity between active objects in a sample could be determined as a graph or other indication of the strength, direction, or other measure of connectivity between the active objects in the sample, based on pairwise metrics determined for the active objects in the sample.

Such measures of connectivity could be determined between neurons, myocytes, or cells that can electrically signal to each other or that are otherwise functionally connected such that changes in activity of a first cell can result, on a time scale of seconds to minutes, in a measureable change in activity in a second cell that is connected to the first cell.

To facilitate such imaging, over periods of time, the samples could be disposed within or proximate to an automated imaging system. Such an automated imaging system could include an imaging device (for example, a microscope, a fluorescence imager, one or more light sources, and/or other elements configured to facilitate imaging samples) and a gantry or other actuator configured to move the imaging device relative to a sample container that contains the samples (e.g., relative to a sample container that has a plurality of wells, each well containing a respective sample of cultured cells, explanted tissue, or some other biological material of interest). The actuator could act, in an automated fashion, to move the imaging device at specified points in time (e.g., according to a scan schedule) to image each of the samples. Accordingly, one or more images could be generated automatically for each of the samples during each of a plurality of scan periods. The samples, within their sample container(s), and the automated imaging system could both be disposed within an incubator, avoiding the necessity of removing the samples from an incubator in order to image them. In such an embodiment, the samples could develop more 'naturally,' avoiding the perturbations that transferring the samples from the incubator to an imaging system may cause.

Operating such a system in such a fashion may produce a plurality of images for a particular sample over time. It can be beneficial to automate certain aspects of the analysis. For example, automated systems (e.g., a server or other controller implementing one or more of the methods described herein) could operate to identify and locate "active objects" within a sample, based on images of the sample. Such active objects may include cells, or portions of cells (e.g., nuclei, mitochondria, or other organelles, cell cytoplasm and/or compartments thereof, dendritic segments or other compartments of a neuron), that vary over time with respect to activity (e.g., with respect to calcium concentration, transmembrane voltage, phosphorylation and/or ubiquitination state, transcriptional or translational activity, or some other image-able proxy for an activity of interest). Such cells may include neurons, smooth muscle cells, striated muscle cells, cardiomyoctyes, secretory epithelial cells, or some other variety of cell that can exhibit image-able increases and decreases in an activity level of interest.

It can be difficult to identify and locate (or "segment") such objects within an image, particularly to identify changes over time. In order to identify and locate such objects, a sequence of images from a scan of a sample can be used to generate a "range image" for the sampled during the scan period. Such a range image is determined by determining the difference, for each location within the image frame of sequence of images, between the maximum and minimum intensity values across all of the images of the sequence. Thus, a 'bright' pixel of the range image corresponds to a location (for example, a location of a cell, or a location of a portion of a cell) that changed, with respect to the imaged activity level (e.g., with respect to a fluorescently-detected intracellular calcium concentration), across the sequence of images. The location, extent, or other information about "active objects" (e.g., cells, portions of cells) within the sample can then be determined from the range image (e.g., via thresholding, template matching, etc.). Such a method has the advantages of discarding regions that are 'always active' (for example, regions that exhibit consistently high but non-varying artefactual levels of autofluorescence) while emphasizing regions that vary with respect to activity, but that are rarely and/or weakly active (for example, a neuron whose activity only bursts once during a scan).

The location, extent, or other information about the identified active objects can then be used to determine information about the active objects. For example, a time-varying activity trace across the scan could be determined for each of the active objects. This time-varying activity trace can be used to determine information about the active object (e.g., a burst rate, an average burst duration or intensity, an overall average intensity, an amount of time spent bursting/exhibiting elevated activity), about a population of active objects (e.g., an overall mean burst duration, a mean burst rate), and/or about relationships between active objects (e.g., a correlation between time-varying activity traces, a degree or pattern of correlation between time-varying activity traces of a set of active objects). Additionally or alternatively, such time-varying activity traces could be used to filter out objects that have been erroneously identified as active objects (e.g., identified using the range image method described above) by rejecting from further analysis identified objects that do not exhibit at least one burst).

II. Example Image Processing

A plurality of images can be generated, using the systems and methods described herein and/or using some other apparatus or methods, of a sample contained within a sample container. The images can be organized, according to the times at which they are generated, into discrete "scans." Each scan is separated in time from the other scans by a specified amount of time (e.g., hours, days, weeks, months), and each scan may include one or more images. For example, each scan could include three minutes' worth of images (or some other suitable duration) of a sample, taken at a rate of three images per second (or at some other suitable rate). The images corresponding to a particular scan can be analyzed in order to determine some information about a sample during the time period of the scan. This can include determining that cells and/or portions thereof within the sample have exhibited some activity during the scan (that they are "active objects"), locating and/or determining the spatial extent of such cells and/or active portions thereof, or determining some other information about the sample. For example, time-varying activity traces could be determined, for each such identified and/or located object, that describe the activity level of the objects over the scan. Such activity levels (or "traces") could be used to determine information about the cells, about populations of cells, about the interrelations between the cells, or some other information about the sample. Such information could be determined for each scan of a number of different scans taken over time, and used to determine some information about the behavior of the sample over time (e.g., over hours, days, weeks, or months).

A variety of image processing techniques may be applied to visible and/or invisible-light images of a sample, taken during a single scan, in order to identify, locate, and/or determine the extent within an image of cells or other objects of interest within the sample. The images taken during a single scan are used to generate a "range image" that emphasizes objects (e.g., cells, portions of cells) that exhibit, during the scan, variations in intensity that correspond to variations in activity level. For example, the images could be fluorescence images taken to detect a fluorescent substance within the sample that corresponds to the activity of interest. Such a fluorescent substance could include a calcium-sensitive fluorophore e.g., where the concentration of intracellular calcium are chosen as a proxy for activity), a voltage sensitive fluorophore (e.g., where variations in trans-membrane voltage are chosen as a proxy for activity), or some other substance that has a fluorescent property (e.g., a fluorescence intensity, a excitation wavelength, an emission wavelength) that is correlated with some activity metric of interest (e.g., phosphorylation/ubiquitination state, transcriptional/translational activity, intracellular calcium concentration, transmembrane voltage). Additionally or alternatively, dyes, chromophores, chemiluminescent substances, or other substances having an optical property (e.g., a color, an opacity, an intensity) that is correlated with some activity metric of interest may be used to facilitate imaging activity during a scan.

Such a range image can be generated for a scan by, for a given pixel of the range image, determining the range of a set of pixel values, across the images in the scan, that correspond to the location of the given pixel of the range image within the image frame of the images of the scan. This can include comparing only those pixels, across the images of the scan, that correspond exactly to the location of the range image pixel. Alternatively, a set of nearby pixels of each of the images may be used to generate the range (e.g., to provide a smoothing or filtering function when determining the range image). Determining the range of such a set of pixel values can include determining the difference between a maximum of the pixel values and a minimum of the pixel values, or may include other methods (e.g., determining a difference between the fifth percentile of pixel values and the ninety-fifth percentile of pixel values, in order to discard outlier pixel values). A range image generated using the methods described herein can emphasize objects, represented within the set of scan images, that vary with respect to intensity across the scan period even when those objects may have been active rarely and/or for very short period(s) of time within the scan period. Further, such a range image can reject and/or de-emphasize objects and/or regions that exhibited consistent high intensity (e.g., due to the presence of confounding autofluorescent substances, or substances that erroneously active a fluorophore or other activity-sensitive contrast agent in the sample) across the scan period, but that did not vary and thus are unlikely to represent active cells, portions of cells, or other active objects of interest.

FIG. 1 illustrates the contents 100 of an example sample container (e.g., contents of a well of a sample container that contains an array of such wells). The contents 100 include a first cell 110a and a second cell 110b (e.g., first and second neurons). The cells 110a, 110b are active cells such that, if imaged multiple times over a scan period, the intensity of light received from the cells (e.g., fluorescent light received from a calcium-sensitive fluorophore expressed by or otherwise present within the cells) varies from image to image across the scan period. The cells 110a, 110b include active areas that may be detected, using the methods described herein, as respective active objects. As shown, the first cell 110a includes a first active object 120a e.g., a nucleus) while the second cell 110a includes a second active object 120b (e.g., a nucleus) and a third active object 120c (e.g., a portion of a dendritic network that exhibits variation, over time, in calcium concentration or in some other activity-related image-able property).

The contents 100 of the sample container can be imaged multiple times, across a scan period, according to the systems and methods described herein and/or via some other apparatus or process. The intensity of the cells and/or of active portions thereof can vary, with the varying activity of those cells and/or portions, across the scan period. Accordingly, the intensity of light received from those cells and/or portions of cells can vary across the scan period and this variation can be captured by the images taken across the scan period. These variations can then be used to generate a range image that can, in turn, be used to identify, locate, or perform some other analysis related to the contents of the sample container.

FIGS. 2A, 2B, 2C, and 2D illustrate first 200a, second 200b, third 200c, and fourth 200d example images, respectively, taken of the contents 100 at respective different first, second, third, and fourth points in time within a scan period. The first active object 120a is active during the first and second points in time, and thus the first 200a and second 200b images show corresponding high-intensity regions, while the corresponding locations of the third 200c and fourth 200d images are relative darker. The second active object 120b was only active during the fourth point in time, while the third active object 120c was active during the first, third, and fourth points in time. Additionally, an artifact 130 emitted light at a consistent intensity across all four points in rime. Accordingly, all four images 200a-d show a corresponding high-intensity region. Such an artifact may be a region that exhibits interfering autofluorescence (e.g., includes a fluorophore that overlaps with respect to excitation spectrum and/or emission spectrum with a fluorophore used to image activity within the sample), a region that contains a high concentration of a contrast agent and/or that includes a substance that increases the fluorescence of the contrast agent (e.g., that binds to and activates a calcium-sensitive fluorophore or a region that emits confounding light through some other mechanism.

A range image 300 can then be generated from the example images 200a-d and/or from additional images taken of the sample contents 100 during the scan period. This range image 300 can be generated according to the systems and/or methods described herein such that the active objects 120a, 120b, 120c are emphasized in the range image 300 (the bright regions). Conversely, regions that did not exhibit changes in intensity over the scan period are not emphasized in the range image (e.g., the region corresponding to the artifact 130). The range image 300 can then be used to identify, locate, and/or determine the extent of active objects within the sample.

Such identification, location, or other segmentation tasks may be accomplished, based on a range image generated as described herein, via a variety of methods. For example, background subtraction, noise filtering, or some other pre-processing methods could be applied to the range image before identifying the location of active objects (e.g., cells, portions of cells) within the range image. Thresholding, template matching, or other methods could then be applied to the range image and/or a pre-processed version thereof in order to locate active objects within the image frame of the range image.

Determining the location of an active object (e.g., the location of a cell, or of a portion of a cell, that exhibits changes, over a scan period, in intracellular calcium concentration or in some other image-able metric of a biological activity of interest) can include determining a single location (e.g., a centroid, an arbitrary point within a boundary of the active object), an effective radius, a region (e.g., a regions defined by a determined perimeters of the active object), a set of pixels or other discrete sub-regions within an image frame, or determining some other location information for each of the active objects. FIG. 4 illustrates a variety of locations, within the image frame 400 of the images 200a-d shown in FIGS. 2A-D, determined for the active objects 120a, 120b, 120c shown in FIG. 1. Determining a location can include determining the location of a single point (e.g., 410a, 410b, 410c) for each active object (e.g., a centroid of discrete or otherwise distinguishable high-intensity regions in the corresponding range image). Additionally or alternatively, determining a location can include determining an extent (e.g., 420a, 420b, 420c), within the image frame that each active object occupies. This could include determining sets of pixels and/or pixel locations of the range image across which each active object extends.

The determined locations of the active objects can then be used to determine information about each of the active objects. For example, time-varying activity levels can be determined, based on the determined locations, for each of the active objects. The time-varying activity level for a particular active objects represents the level of activity, as represented by intensity in the images taken of the sample containing the active object (e.g., intracellular calcium concentration), of the active object across a scan. Thus, the time-varying activity level can be used to assess the overall level, pattern, and timing (e.g., relative to other active objects) of activity (e.g., firing of action potentials of a neuron or portion thereof) of the active object. For example, a burst rate or frequency, a burst duration, a burst intensity, an average activity level, a variability of activity level, or some other information and or distribution thereof about the activity of an active abject may be determined from the time-varying activity level determined for the active object. Such information may also be used to determine overall metrics for a sample, e.g., a mean overall activity of active objects in a sample could be determined from the time-varying activity levels for the active objects in the sample.

The determined time-varying activity levels may also be used to determine information about the functional connectivity between active objects (e.g., neurons) within the sample. For example, pairwise correlations may be determined for each pair of active objects in a sample. Such correlations may then be reported and/or used to determine a pattern or an overall degree of coordination between the activities of active objects within a sample.

A time-varying activity level can be generated, for a particular active object, in a variety of ways. In examples wherein determining the location of the active object included determining a set of pixels or some other information about the extent, within an image frame, of the active object, determining the time-varying activity level for the active object could include determining a sum, an average, or some other measure of the overall intensity of the pixels, for each fluorescence intensity image across a scan, that correspond to the extent of the active object (e.g., the determined set of pixels that correspond to the active object). In another example, a weighted average of pixels within a specified distance of a determined point location of an active object may be used to determine the time-varying activity level of the active object across a scan.

Fluorescent imaging of a sample can result in photobleaching of the sample. Such photobleaching can manifest, in fluorescent images taken of the sample, as a gradual decrease in the detected fluorescence intensity of the sample and/or active objects therein over time. This photobleaching can be detected and/or quantified and its effects (e.g., on time-varying activity traces generated from such fluorescence images) reduced or removed in a variety of ways. FIG. 5A illustrates an example of a time-varying activity trace 500 determined for an active object that exhibited photobleaching. The downward trend in the time-varying activity trace 500 caused by the photobleaching is indicated by the dotted line 510. The level of this photobleaching effect can be determined from the time-varying activity trace 500, e.g., by applying a low-pass filter, by applying a moving-window minimum, by identifying and removing discrete bursts, or by employing some other method. The determined level of photobleaching can then be applied to compensate for the effects of photobleaching, generating a more accurate time-varying activity level for an active object (shown by way of example in FIG. 5B as the corrected time-varying activity level 520). Additionally or alternatively, the level of photobleaching over time may be determined in some other method (e.g., by determining, for each fluorescence activity image of a scan, a respective level of photobleaching) and applied to correct one or more time-varying activity levels (shown by way of example in FIG. 5C as the photobleaching level 530).

The range image method described above can be used to identify and/or locate active objects within a sample. Additionally or alternatively, such objects may be identified based on their exhibiting one or more distinct bursts across a scan. For example, the location of a putative active object may be determined (e.g., using the range method described above and/or using some other segmentation method) and this determined location used to determine, for the putative active object, a time-varying activity level. This time-varying activity level can then be analyzed to determine whether the time-varying activity level contains at least one burst. If so, the putative active object can be confirmed and used for additional analysis (e.g., mean burst rates, overall population burst rates, determining the degree and/or pattern of connectivity between confirmed active objects within a sample). If no bursts are detected, the putative active object can be rejected and its time-varying activity trace discarded from additional analysis. A subset of active objects can thus be selected, from a population of putative active objects, that exhibit bursts and are therefore more likely to represent actual active cells and/or portions thereof. Such a selection process can have benefits where, e.g., one or more putative active objects are detected, in a range image, that do not exhibit bursts but instead exhibit artefactual high levels of photobleaching over a scan and thus may appear as high-intensity regions within the range image.

Bursts include any fast change in the detected activity of a cell, portion of a cell, or other active object during a scan period. For example, a burst can result in a fast change in the detected fluorescence intensity of an active object in a recorded video sequence. Such a burst results in a peak in the time-varying intensity level trace determined for the active object. Bursts can be identified, within a given time-varying activity level, using a variety of different methods. In some examples, a burst can be identified within a time-varying activity level wherever the time: varying activity level exceeds a threshold and/or wherever the time-varying activity level increases from a baseline level (e.g., determined from the time-varying activity level trace using a moving-window minimum) by more than a threshold level and/or increases by greater than a threshold rate. Additionally or alternatively, template matching, highpass filtering, or other methods could be used to identify bursts within a time-varying activity level determined as described herein. The strength and duration properties of such burst peaks can be calculated from the active object's time-varying activity level trace. The mean burst properties can be calculated per active object and then aggregated for the all the active objects in a sample during a scan.

III. Example Systems

An automated imaging system may be employed to generate, in an automated fashion, images (e.g., fluorescence activity images) of a plurality of biological samples, in respective wells of a sample container, during a plurality of different scan periods over time. A set of images could be taken, by the automated imaging system, of each sample during each of the scan periods, e.g., a set of images taken at a rate of three images per second over a three minute scan period. The images can then be analyzed in order to determine some information about the samples, e.g., according to the methods described herein.

Use of such an automated imaging system can significantly reduce the personnel costs of imaging biological samples, as well as increasing the consistency, with respect to timing, positioning, and image parameters, of the images generated when compared to manual imaging. Further, such an automated imaging system can be configured to operate within an incubator, removing the need to remove the samples from an incubator for imaging. Accordingly, the growth environment for the samples can be maintained more consistently. Additionally, where the automated imaging system acts to move a microscope or other imaging apparatus relative to the sample containers (instead of, e.g., moving the sample container to be imaged by a static imaging apparatus), movement-related perturbation of the samples can be reduced. This can improve the growth and development of the samples and reduce movement-related confounds.

Such an automated imaging system can operate to generate one or more images during scans that are separated by more than twenty-four hours, by more than three days, by more than thirty days, or by some longer period of time. The scans could be specified to occur at a specified rate, e.g., once per daily, more than daily, more than twice daily, or more than three times daily. The scans could be specified such that at least two, at least three, or some greater number of scans occurs within a twenty-four hour period. In some examples, data from one or more scans could be analyzed (e.g., according to the methods described herein) and used to determine the timing of additional scans (e.g., to increase a rate, duration, image capture rate, or some other property of the scans in order to detect the occurrence of a discrete event that is predicted to occur within a sample).

The use of such an automated imaging system can facilitate imaging of the same biological sample at multiple points in time over long time periods. Accordingly, the development and/or behavior of individual cells and/or networks of cells can be analyzed over time. For example, a set of cells, portions of cells, or other active objects could be identified, within a single sample, within scans taken during different, widely spaced periods of time. These sets of identified objects could then be compared between scans in order to identify the same active object(s) across the scans. Thus, the behavior of individual cells, or portions of cells, can be tracked and analyzed across hours, days, weeks, or months.

Figure 6:
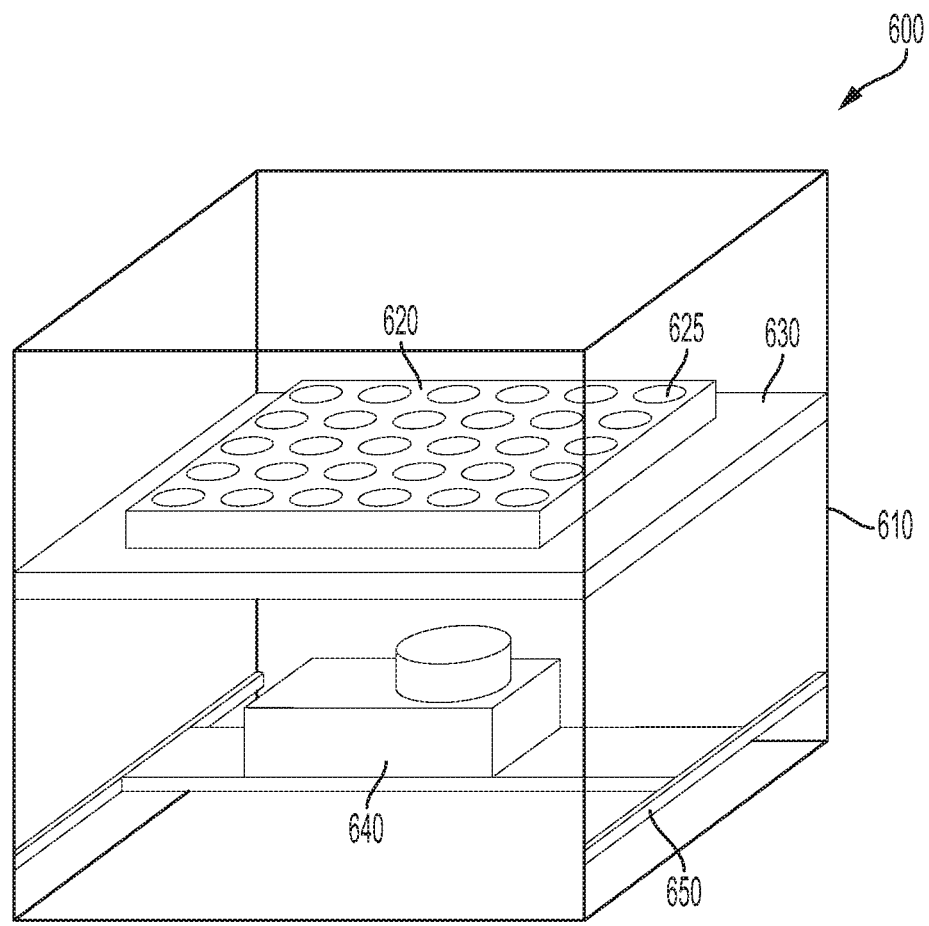
FIG. 6 depicts elements of an example automated sample imaging device.

FIG. 6 illustrates elements of such an automated imaging system 600. The automated imaging system 600 includes a frame 610 to which other elements of the automated imaging system 600 are attached. The frame 610 may be configured (e.g., sized) in order to fit within an incubator. The automated imaging system 600 includes a sample container 620 that is removably placed within a sample container tray 630 that is coupled to the frame 610. The sample container tray 630 could be removable and/or could include removable insert to facilitate holding a variety of different sample containers (e.g., a variety of industry-standard sample containers). The system 600 additionally includes an actuated gantry 650 configured to position an imaging apparatus 640 relative to the sample container 620 such that the imaging apparatus 640 can operate to generate images of the contents of individual wells of the sample container 620 (e.g., the example well 625).

The imaging apparatus 640 can include a microscope, a fluorescence imager, a two-photon imaging system, a phase-contrast imaging system, one or more illumination sources, one or more optical filters, and/or other elements configured to facilitate imaging samples contained within the sample container 620. In some examples, the imaging apparatus 640 includes elements disposed on both sides of the sample container 620 (e.g., a source of coherent, polarized, monochromatic, or otherwise-specified illumination light in order to facilitate, e.g., phase contrast imaging of biological samples). In such examples, elements on both sides of the sample container 620 may be coupled to respective different gantries, to the same gantry, and/or elements on one side of the sample container 620 may not be movable relative to the sample container 620.

The actuated gantry 650 is coupled to the frame 610 and the imaging apparatus 640 and configured to control the location of the apparatus 640 in at least two directions, relative to the sample container 620, in order to facilitate imaging of a plurality of different samples within the sample container 620. The actuated gantry 650 may also be configured to control the location of the imaging apparatus 640 in a third direction, toward and away from the sample container 620, in order to facilitate controlling the focus of images generated using the imaging apparatus 640 and/or to control a depth of material, within the sample container 620, that can be imaged using the imaging apparatus 640. Additionally or alternatively, the imaging apparatus 640 may include one or more actuators to control a focal distance of the imaging apparatus 640.

The actuated gantry 650 may include elements configured to facilitate detection of the absolute and/or relative location of the imaging apparatus 640 relative to the sample container 620 (e.g., to particular well(s) of the sample container 620). For example, the actuated gantry 650 may include encoders, limit switches, and/or other location-sensing elements. Additionally or alternatively, the imaging apparatus 640 or other elements of the system may be configured to detect fiducial marks or other features of the sample container 620 and/or of the sample container tray 630 in order to determine the absolute and/or relative location of the imaging apparatus 640 relative to the sample container 620.

Computational functions (e.g., functions to operate the actuated gantry 650 and/or imaging apparatus 640 to image samples within the sample container 620 during specified periods of time, to generate a range image and/or to perform some other method described herein) may be performed by one or more computing systems. Such a computing system may be integrated into an automated imaging system (e.g., 600), may be associated with such an automated imaging system (e.g., by being connected via a direct wired or wireless connection, via a local network, and/or via a secured connection over the internet), and/or may take some other form (e.g., a cloud computing system that is in communication with an automated imaging system and/or that has access to a store of images of biological samples). Such a computing system may include a communication interface, a user interface, a processor, and data storage, all of which may be communicatively linked together by a system bus, network, or other connection mechanism.

The communication interface may function to allow the computing system to communicate, using analog or digital modulation of electric, magnetic, electromagnetic, optical, or other signals, with other devices, access networks, and/or transport networks. Thus, communication interface may facilitate circuit-switched and/or packet-switched communication, such as plain old telephone service (POTS) communication and/or Internet protocol (OP) or other packetized communication. For instance, communication interface may include a chipset and antenna arranged for wireless communication with a radio access network or an access point. Also, communication interface may take the form of or include a wireline interface, such as an Ethernet, Universal Serial Bus (USB), or High-Definition Multimedia Interface (HDMI) port. Communication interface 402 may also take the form of or include a wireless interface, such as a WiFi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface. Furthermore, communication interface may comprise multiple physical communication interfaces (e.g., a WiFi interface, a BLUETOOTH® interface, and a wide-area wireless interface).

In some embodiments, the communication interface may function to allow computing system to communicate with other devices, remote servers, access networks, and/or transport networks. For example, the communication interface may function to transmit and/or receive an indication of images of biological samples (e.g., fluorescence activity images), to transmit an indication of a range image, a set of locations of active objects within such images, and/or time-varying activity traces determined from such active objects generated from such images using the methods described herein, or some other information.

The user interface of such a computing system may function to allow computing system to interact with a user, for example to receive input from and/or to provide output to the user. Thus, user interface may include input components such as a keypad, keyboard, touch-sensitive or presence-sensitive panel, computer mouse, trackball, joystick, microphone, and so on. User interface may also include one or more output components such as a display screen which, for example, may be combined with a presence-sensitive panel. The display screen may be based on CRT, LCD, and/or LED technologies, or other technologies now known or later developed. User interface may also be configured to generate audible output(s), via a speaker, speaker jack, audio output port, audio output device, earphones, and/or other similar devices.

In some embodiments, user interface may include a display that serves to present video or other images to a user (e.g., video of images generated during a particular scan of a particular biological sample). Additionally, user interface may include one or more buttons, switches, knobs, and/or dials that facilitate the configuration and operation of the computing device. It may be possible that some or all of these buttons, switches, knobs, and/or dials are implemented as functions on a touch- or presence-sensitive panel. The user interface may permit a user to specify the types of samples contained within an automated imaging system, to specify a schedule for imaging of the samples, to specifying parameters of image segmentation and/or analysis to be performed by the system, or to input some other commands or parameters for operation of an automated imaging system.

In some examples, portions of the methods described herein could be performed by different devices, according to an application. For example, different devices of a system could have different amounts of computational resources (e.g., memory, processor cycles) and different information bandwidths for communication between the devices. For example, a first device could be an embedded processor(s) that could operate an actuated gantry, imaging apparatus, or other elements to generate images of biological samples during a plurality of different scan periods. A second device could then receive (e.g., via the internet, via a dedicated wired link), from the first device, image information from the first device and perform the image processing and analysis methods described herein on the received image data. Different portions of the methods described herein could be apportioned according to such considerations.

IV. Example Methods

Figure 7:
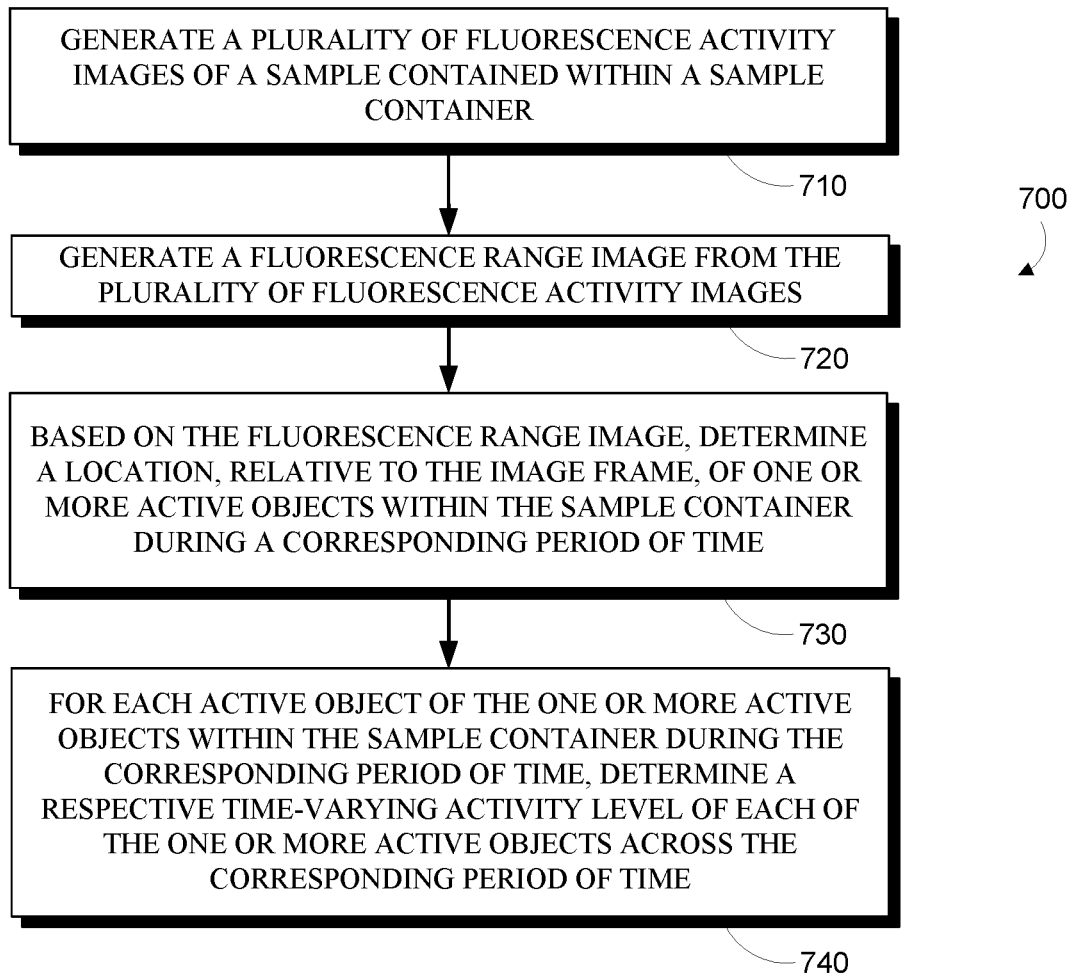
FIG. 7 is a flowchart of an example method.

FIG. 7 is a flowchart of a method 700 for identifying biologically active cells during one or more periods of time. The method 700 includes, for each of the one or more periods of time, generating a plurality of fluorescence activity images of a sample contained within a sample container (710). The sample includes biologically active cells, and each image of the plurality of fluorescence activity images includes a respective plurality of pixel values, each pixel value corresponding to a respective pixel location within an image frame. The method 700 additionally includes, for each of the one or more periods of time, generating a fluorescence range image from the plurality of fluorescence activity images (720). Generating a fluorescence range image from a plurality of fluorescence activity images includes determining a plurality of pixel values for the fluorescence range image and determining a given pixel value for the fluorescence range image includes determining a range of a set of pixel values, from each of the plurality of fluorescence activity images, that have pixel locations corresponding to a pixel location of the given pixel value within the image frame.

The method 700 additionally includes, for each of the one or more periods of time, based on the fluorescence range image, determining a location, relative to the image frame, of one or more active objects within the sample container during a corresponding period of time (730). Each of the one or more active objects is a portion of at least one respective biologically active cell present within the sample during the corresponding period of time. The method 700 further includes, for each of the one or more periods of time and for each active object of the one or more active objects within the sample container during each corresponding period of time, determining a respective time-varying activity level of each of the one or more active objects across the corresponding period of time (740). This can include determining each time-varying activity level based on a set of pixel values, from each of the plurality of fluorescence activity images, that have pixel locations proximate to the determined location of a corresponding active object.

Figure 8:
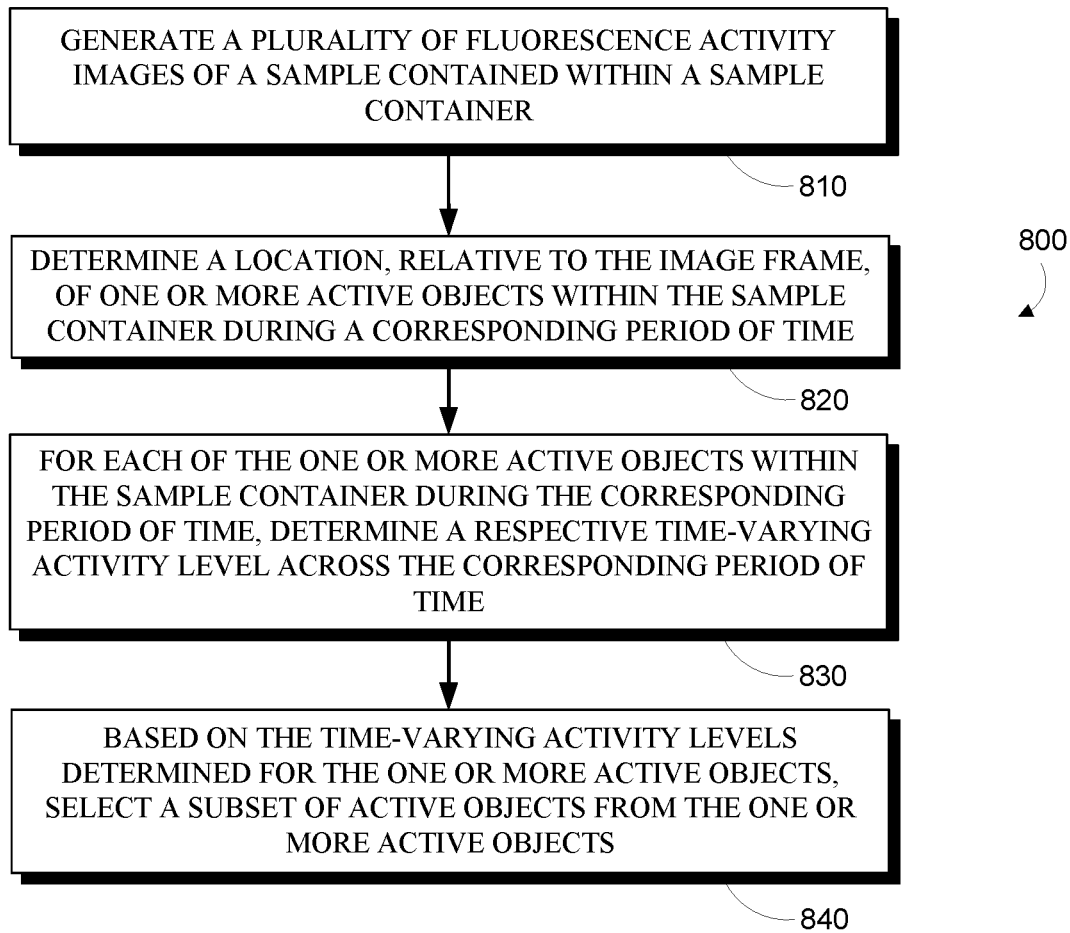
FIG. 8 is a flowchart of an example method.
Figure 9:
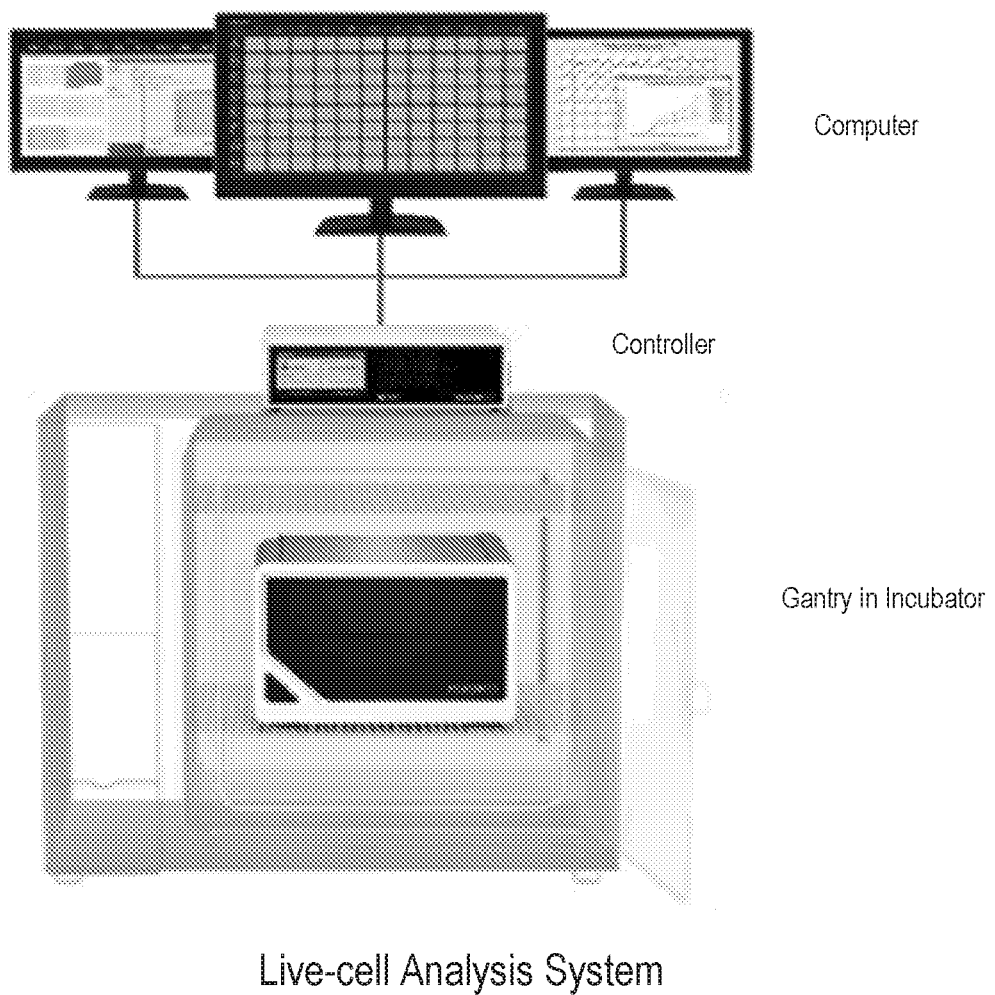
FIG. 9 is an image of an example imaging and analysis system.
Figure 12:
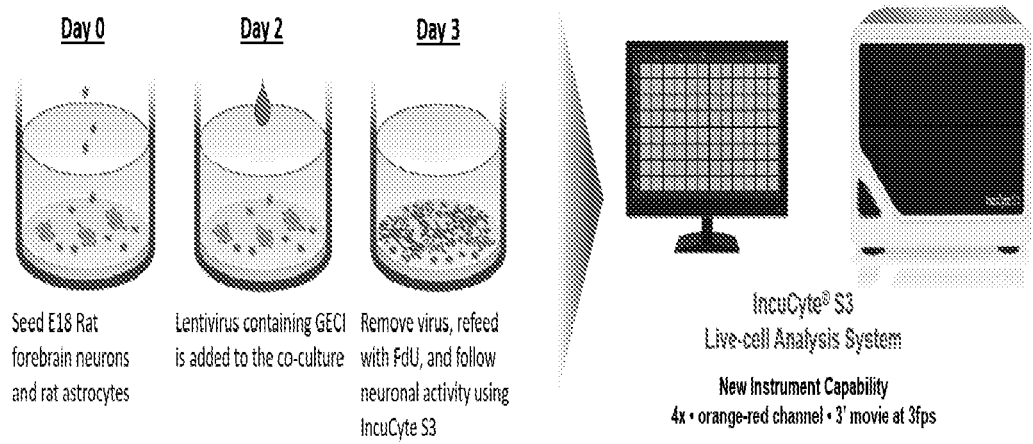
FIG. 12 depicts an example progression of development of a sample over time.
Figure 13A:
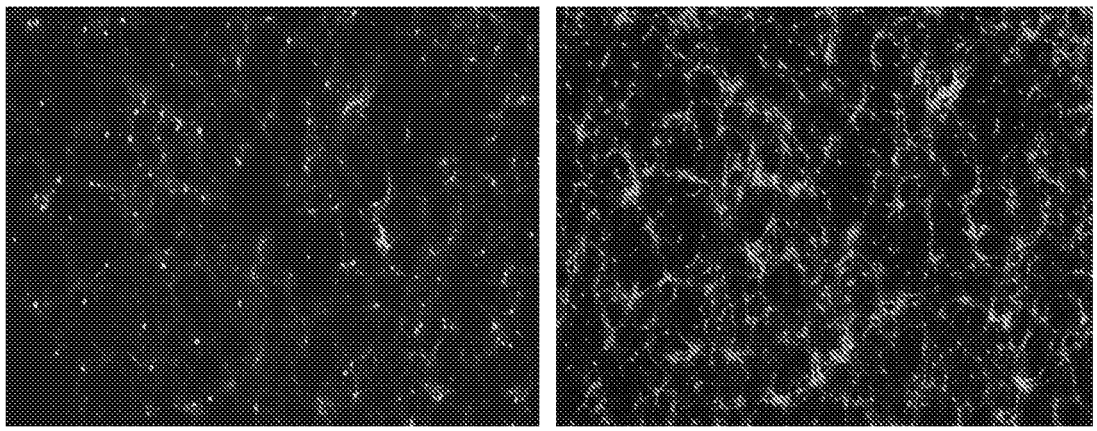
FIG. 13A depicts example experimental results obtained using the systems and methods depicted herein.
Figure 13B:
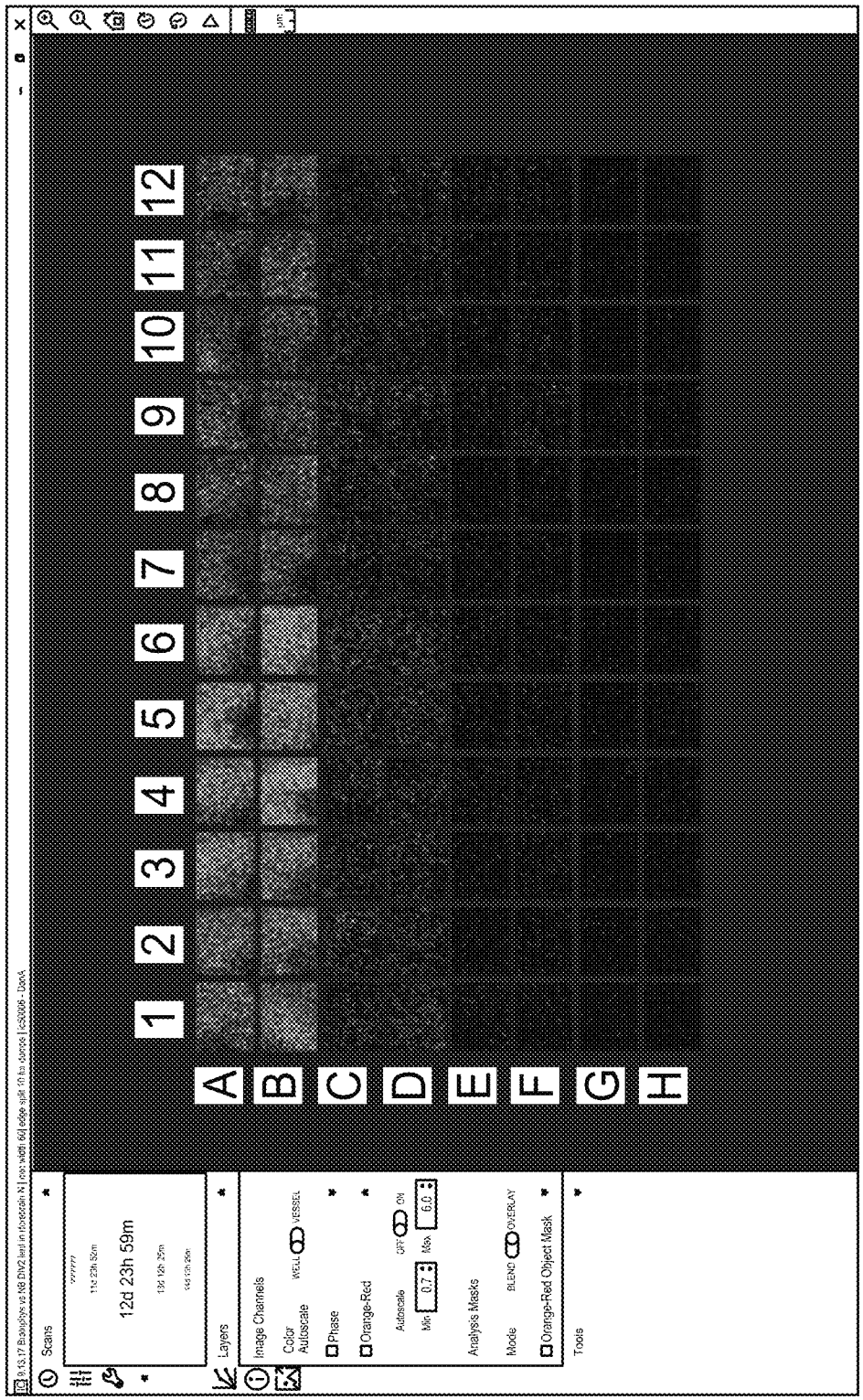
FIG. 13B depicts example experimental results obtained using the systems and methods depicted herein.
Figure 13E:
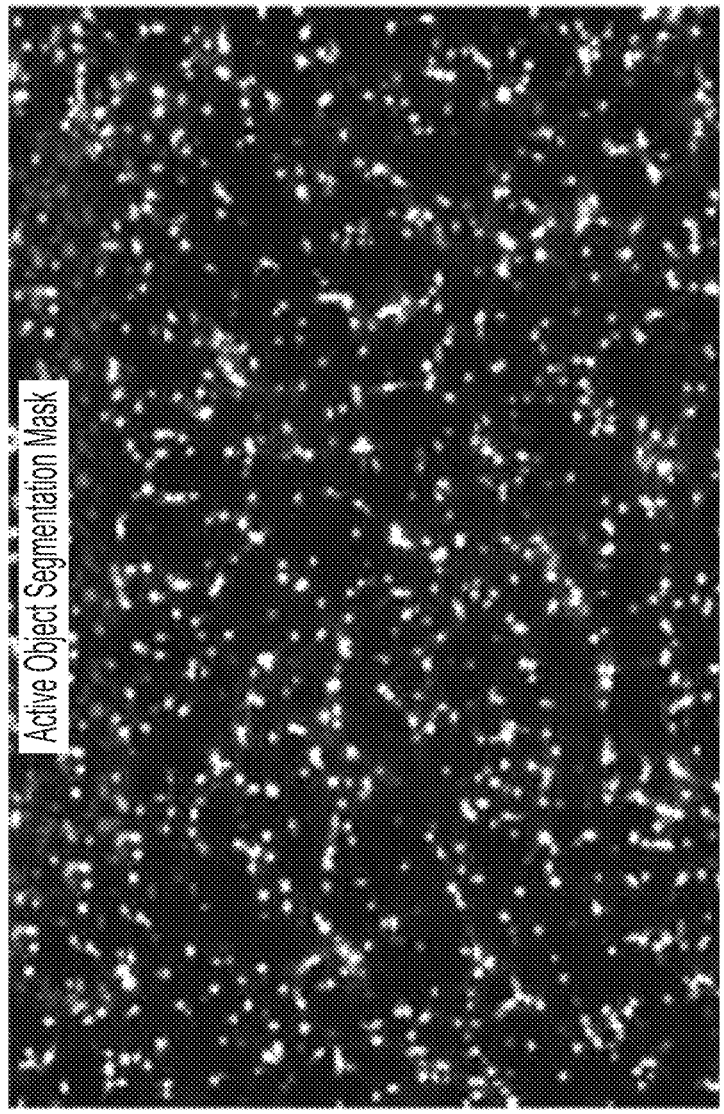
FIG. 13E depicts example experimental results obtained using the systems and methods depicted herein.
Figure 13F:
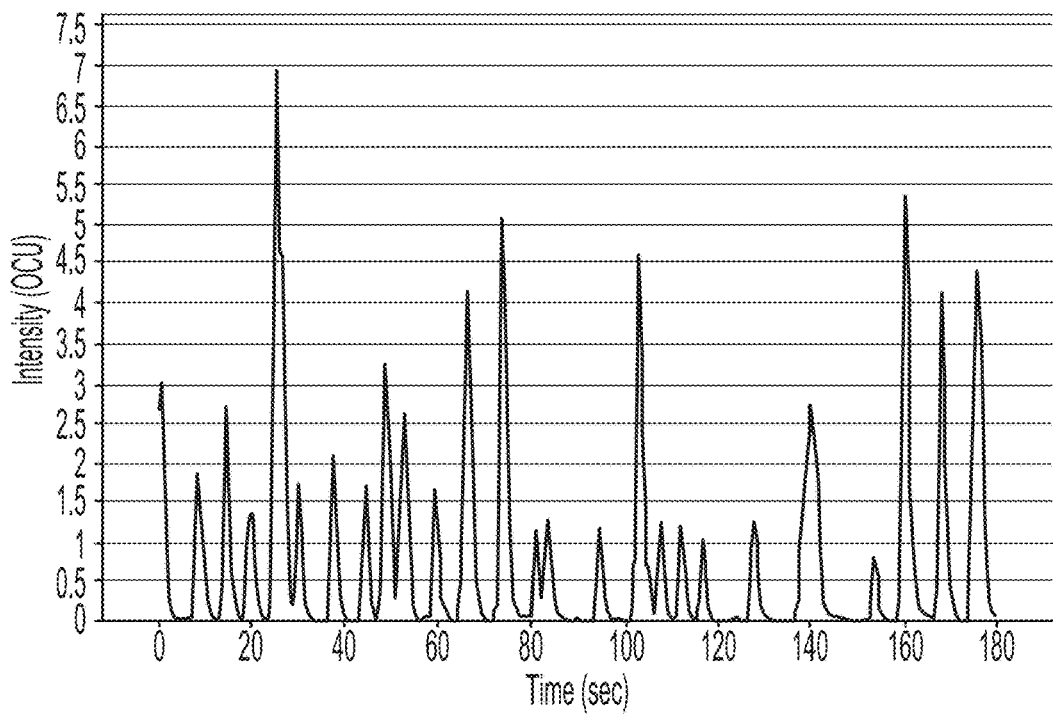
FIG. 13F depicts example experimental results obtained using the systems and methods depicted herein.
Figure 13G:
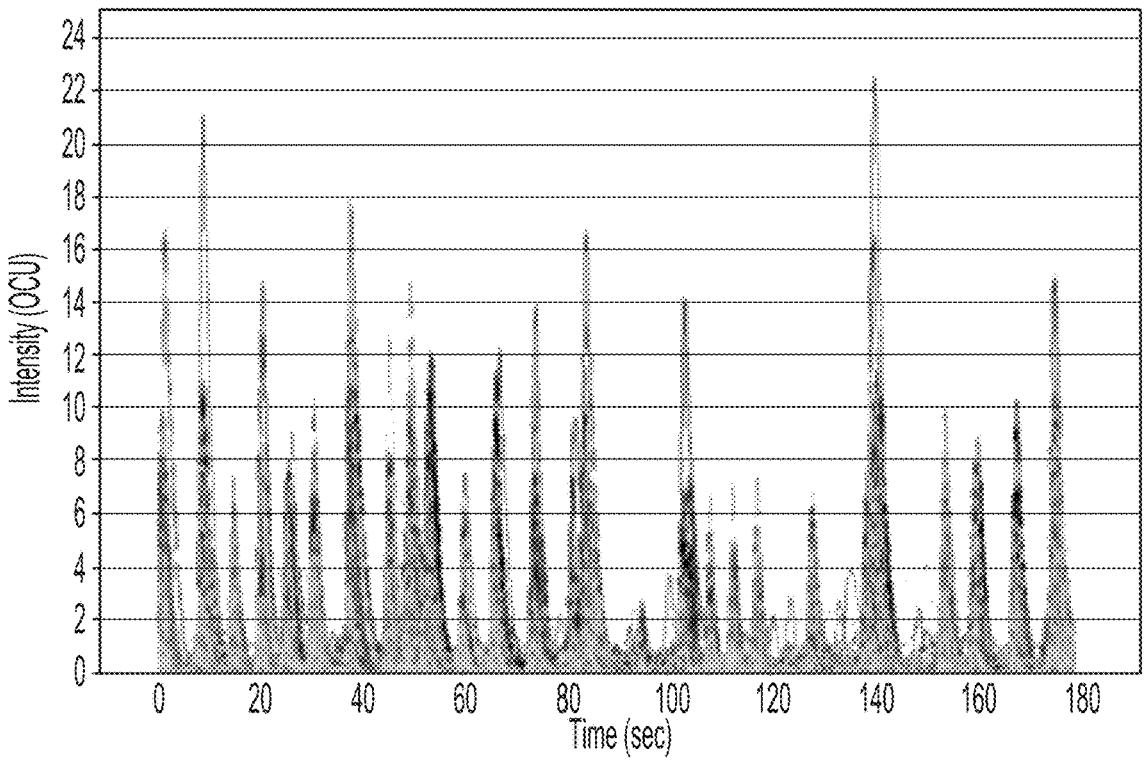
FIG. 13G depicts example experimental results obtained using the systems and methods depicted herein.
Figure 13H:
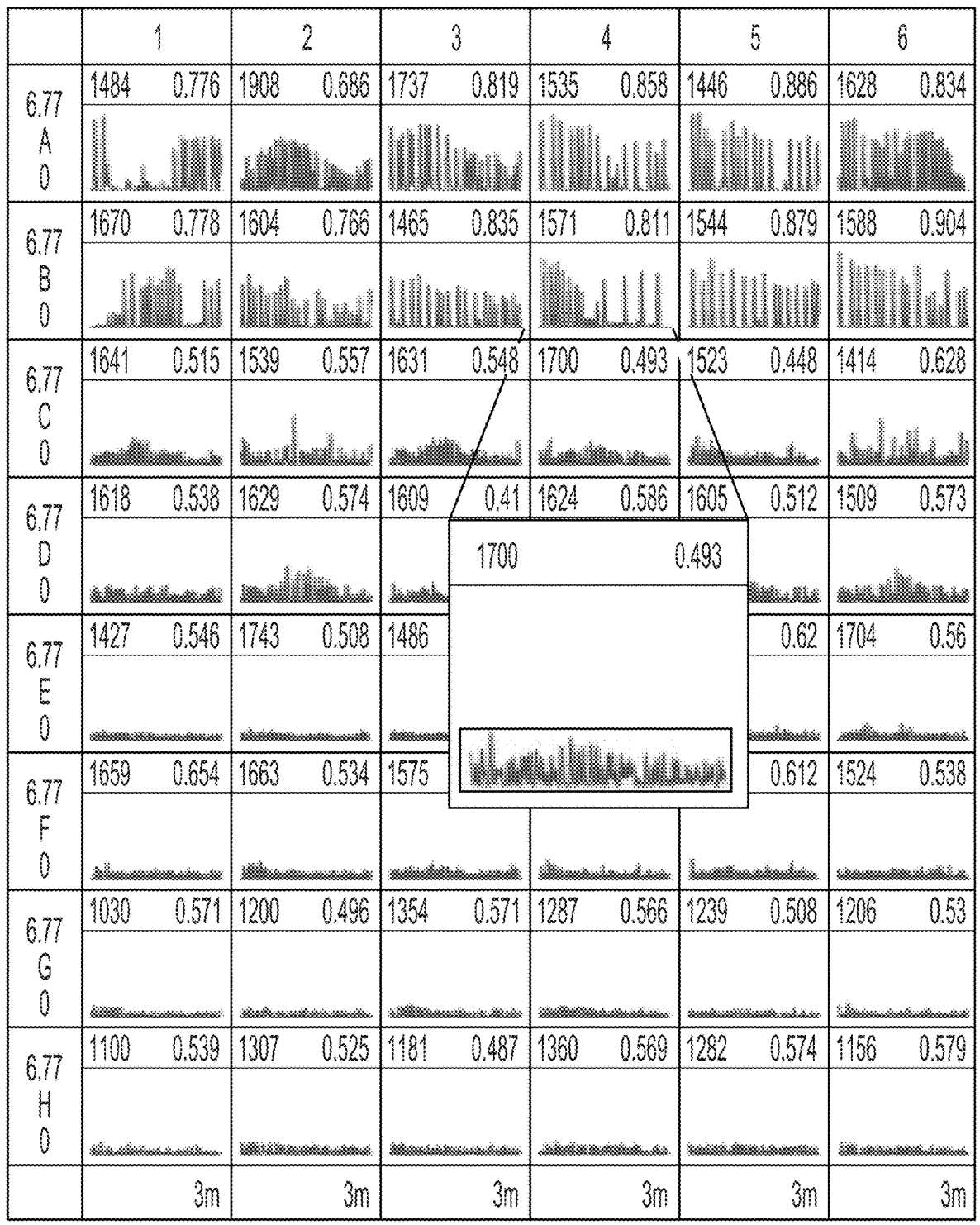
FIG. 13H depicts example experimental results obtained using the systems and methods depicted herein.
Figure 13M:
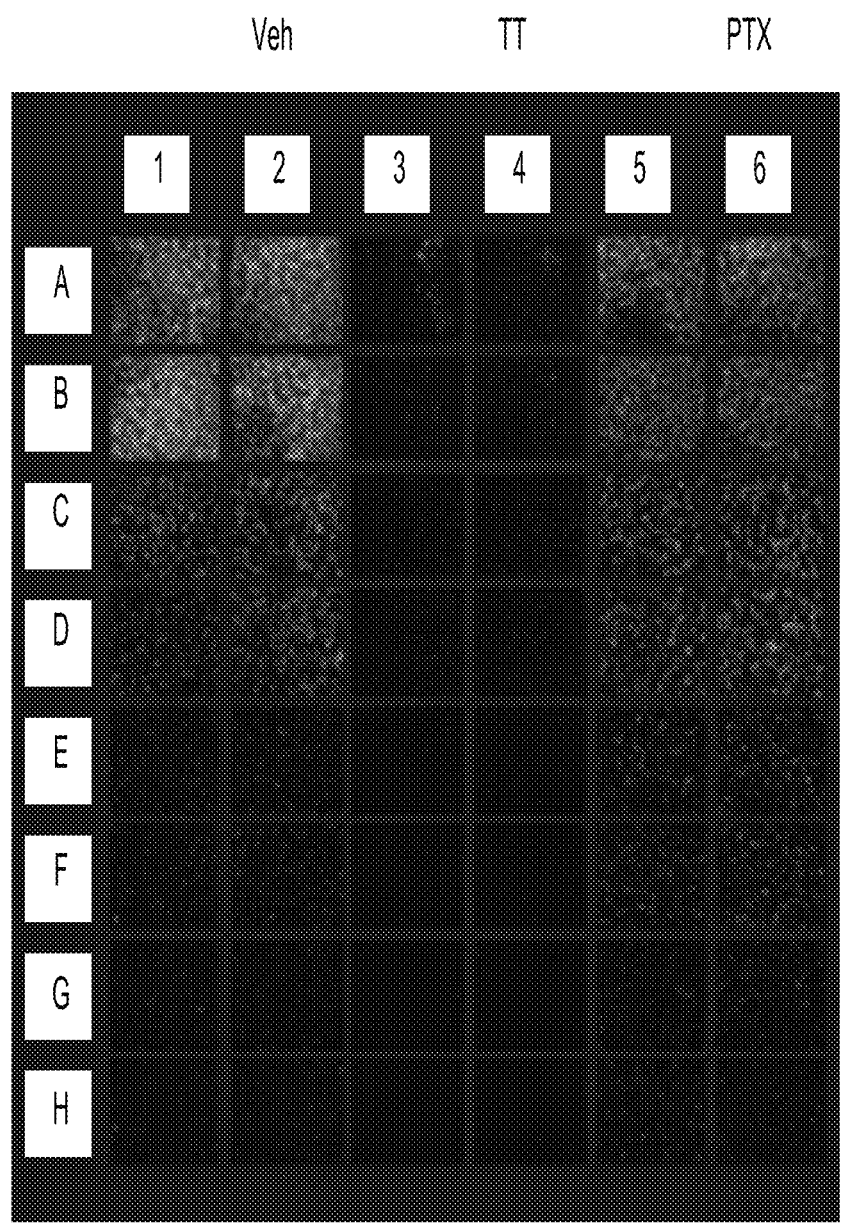
FIG. 13M depicts example experimental results obtained using the systems and methods depicted herein.
Figure 13N:
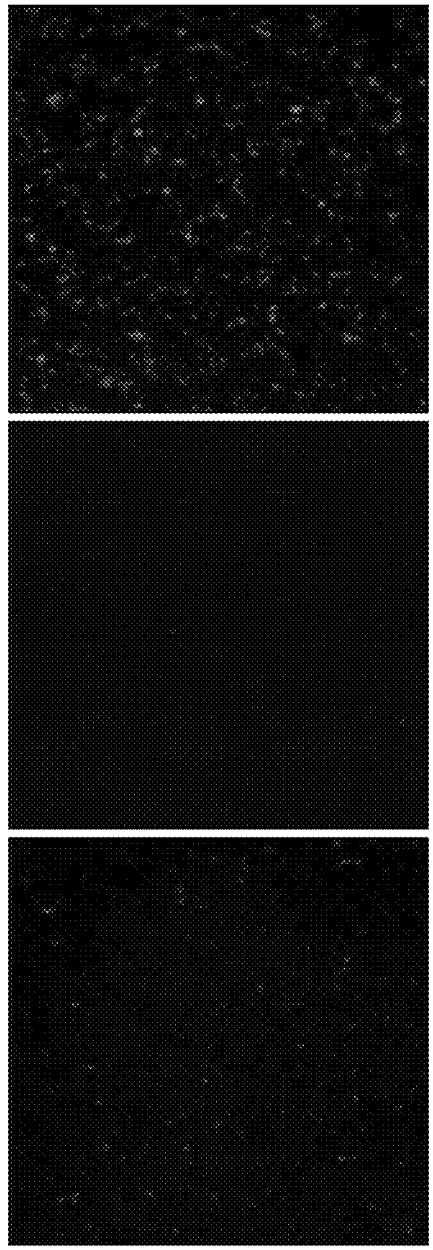
FIG. 13N depicts example experimental results obtained using the systems and methods depicted herein.
Figure 13O:
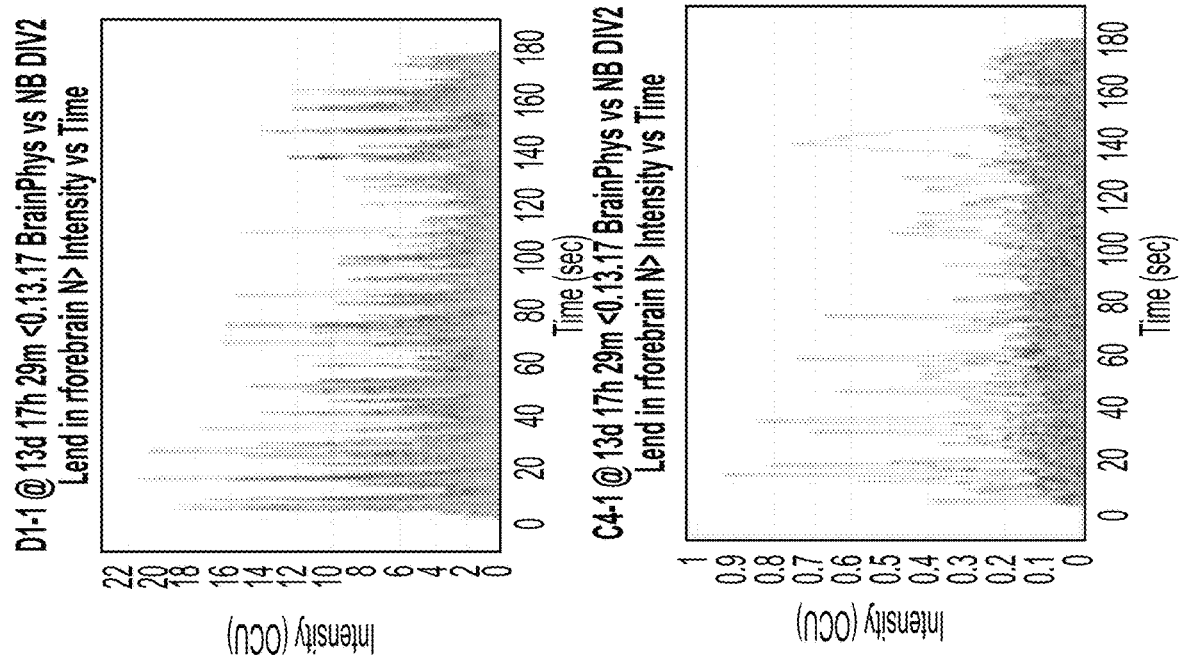
FIG. 13O depicts example experimental results obtained using the systems and methods depicted herein.
Figure 14:
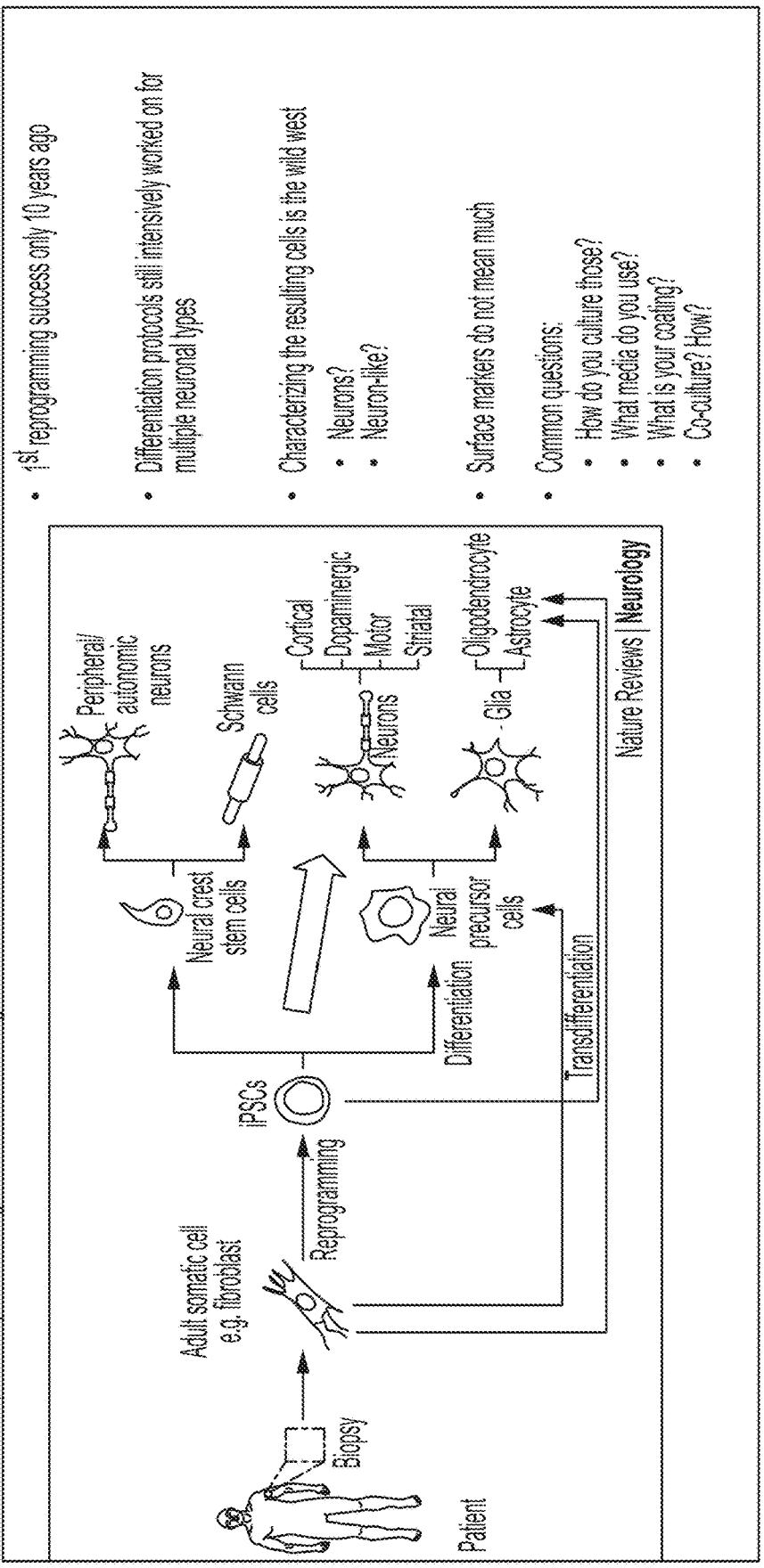
FIG. 14 depicts differentiation of cells.
Figure 15:
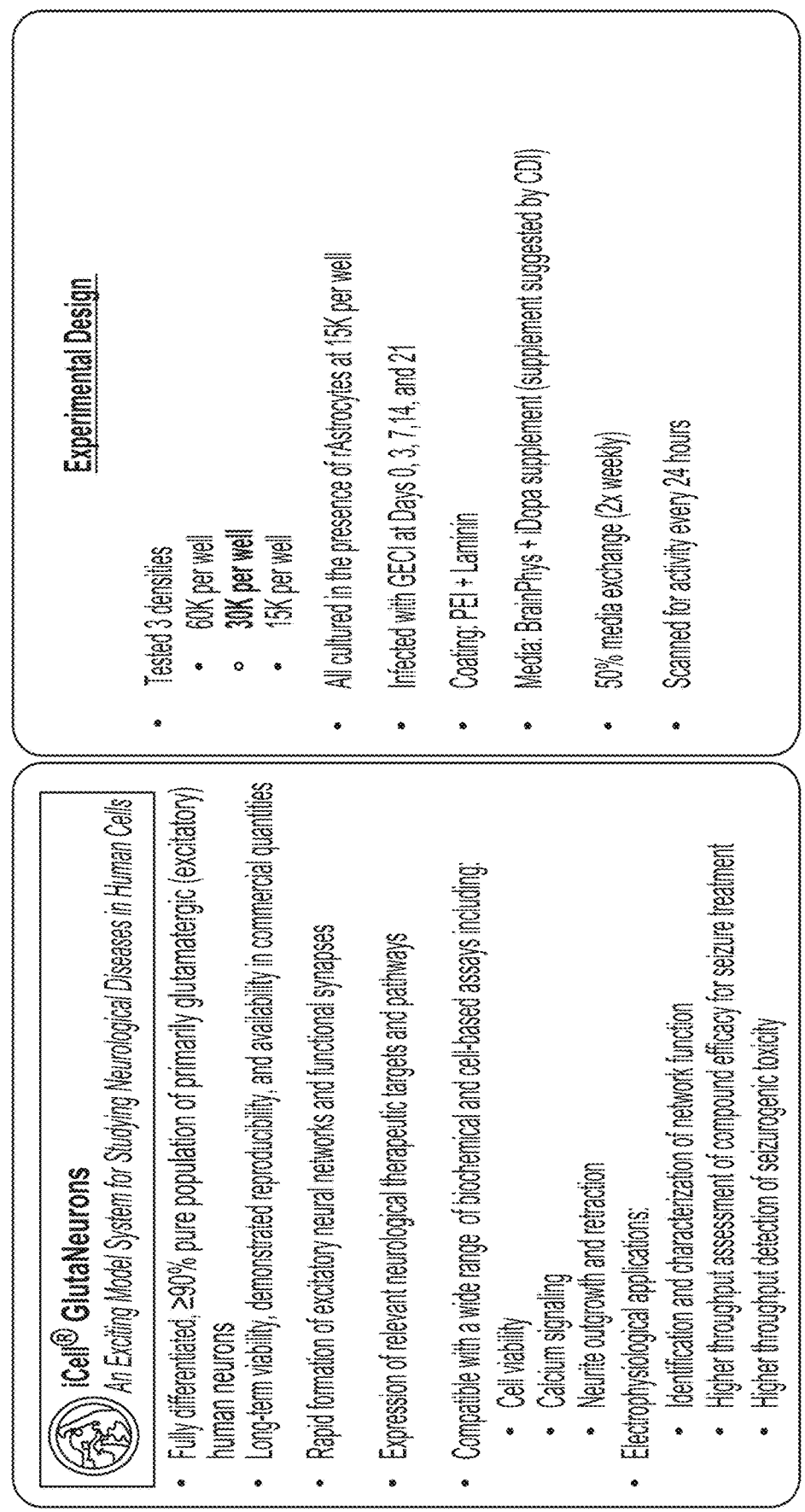
FIG. 15 depicts the capabilities of systems as described herein.
Figure 16A:
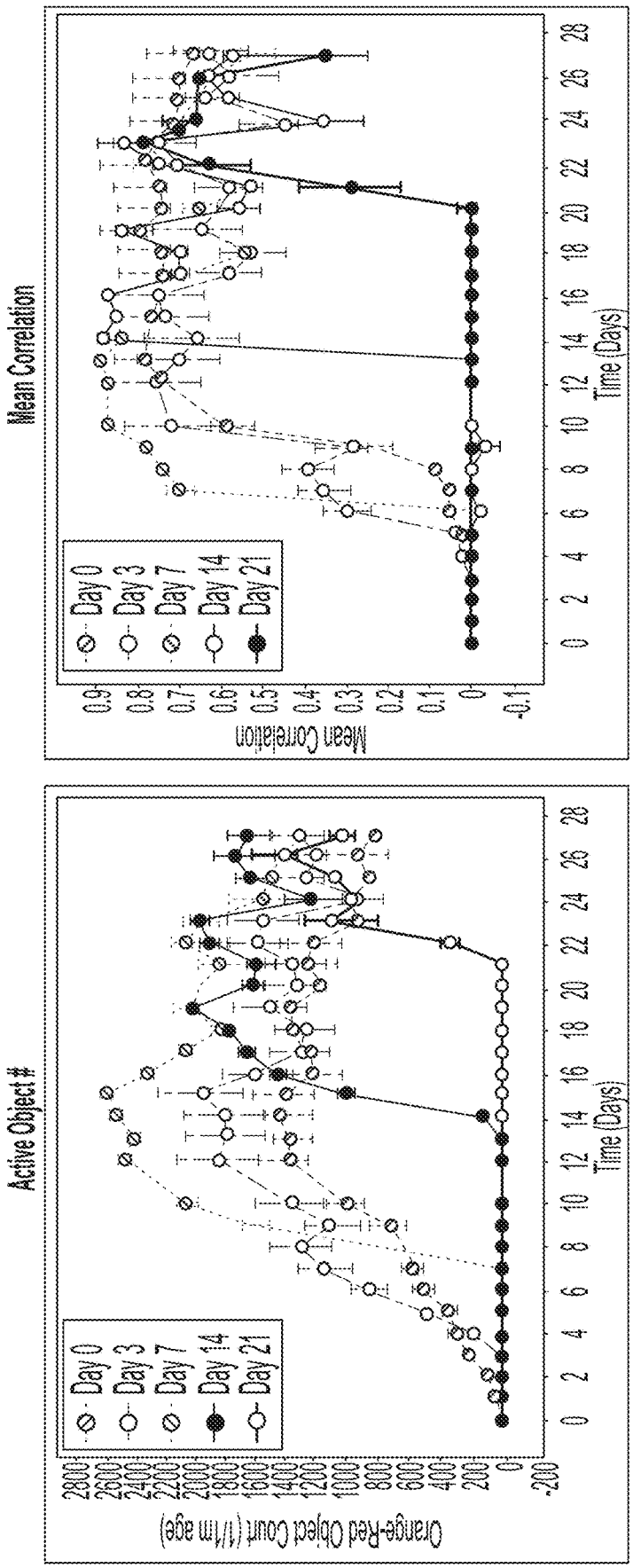
FIG. 16A depicts example experimental results obtained using the systems and methods depicted herein.
Figure 16B:
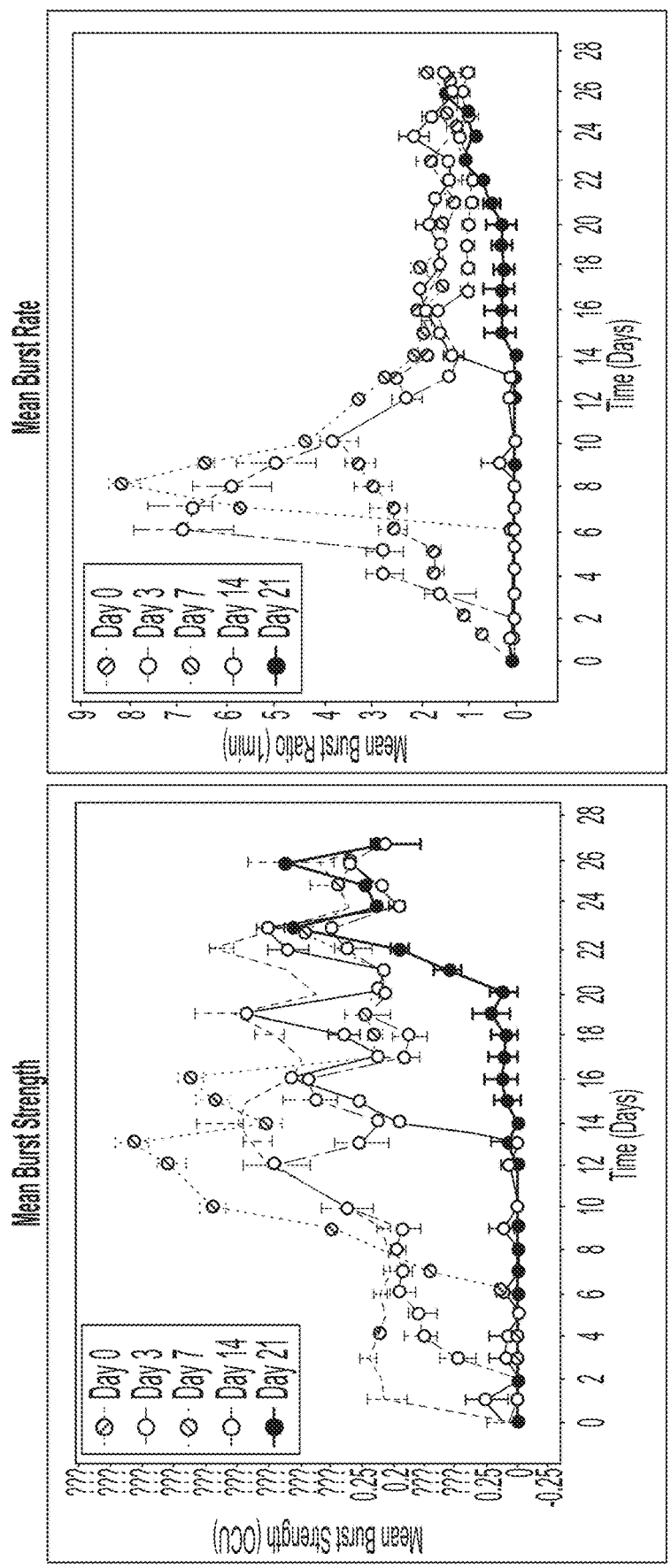
FIG. 16B depicts example experimental results obtained using the systems and methods depicted herein.
Figure 16C:
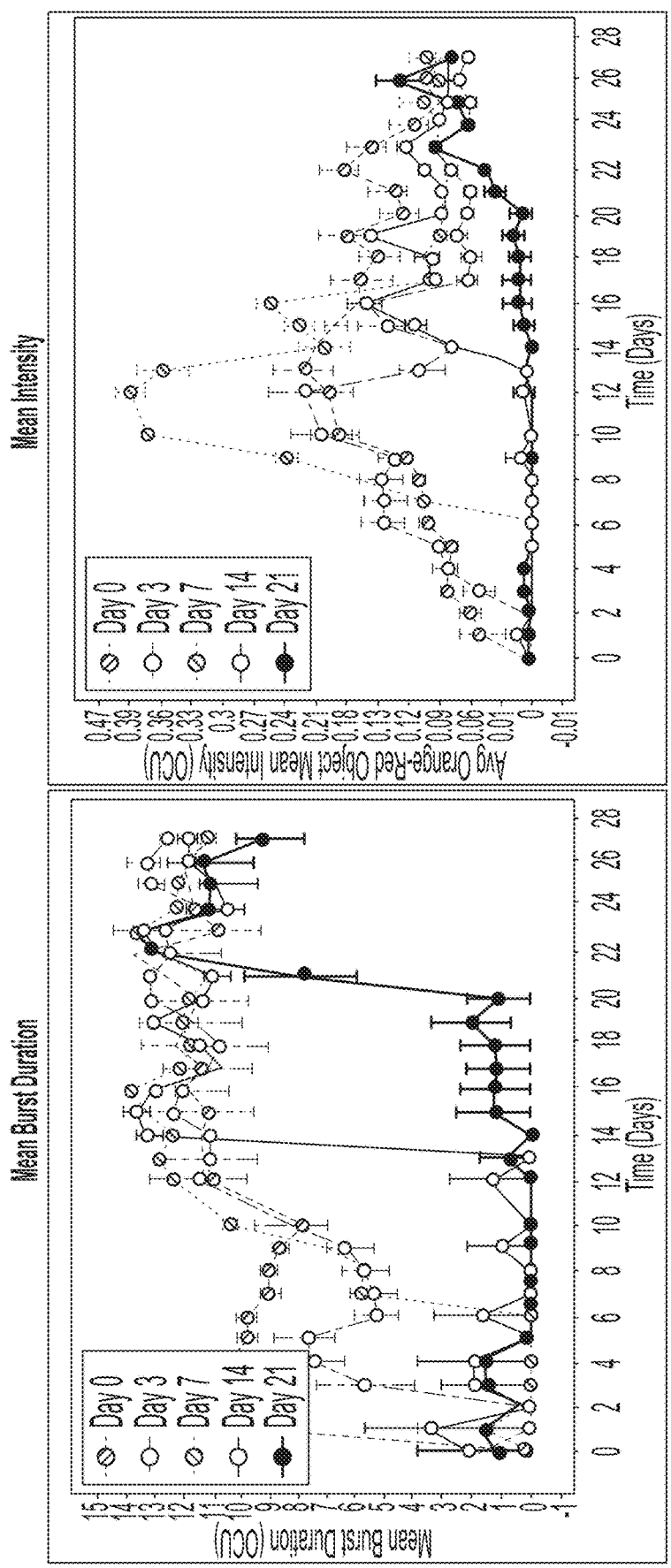
FIG. 16C depicts example experimental results obtained using the systems and methods depicted herein.
Figure 16D:
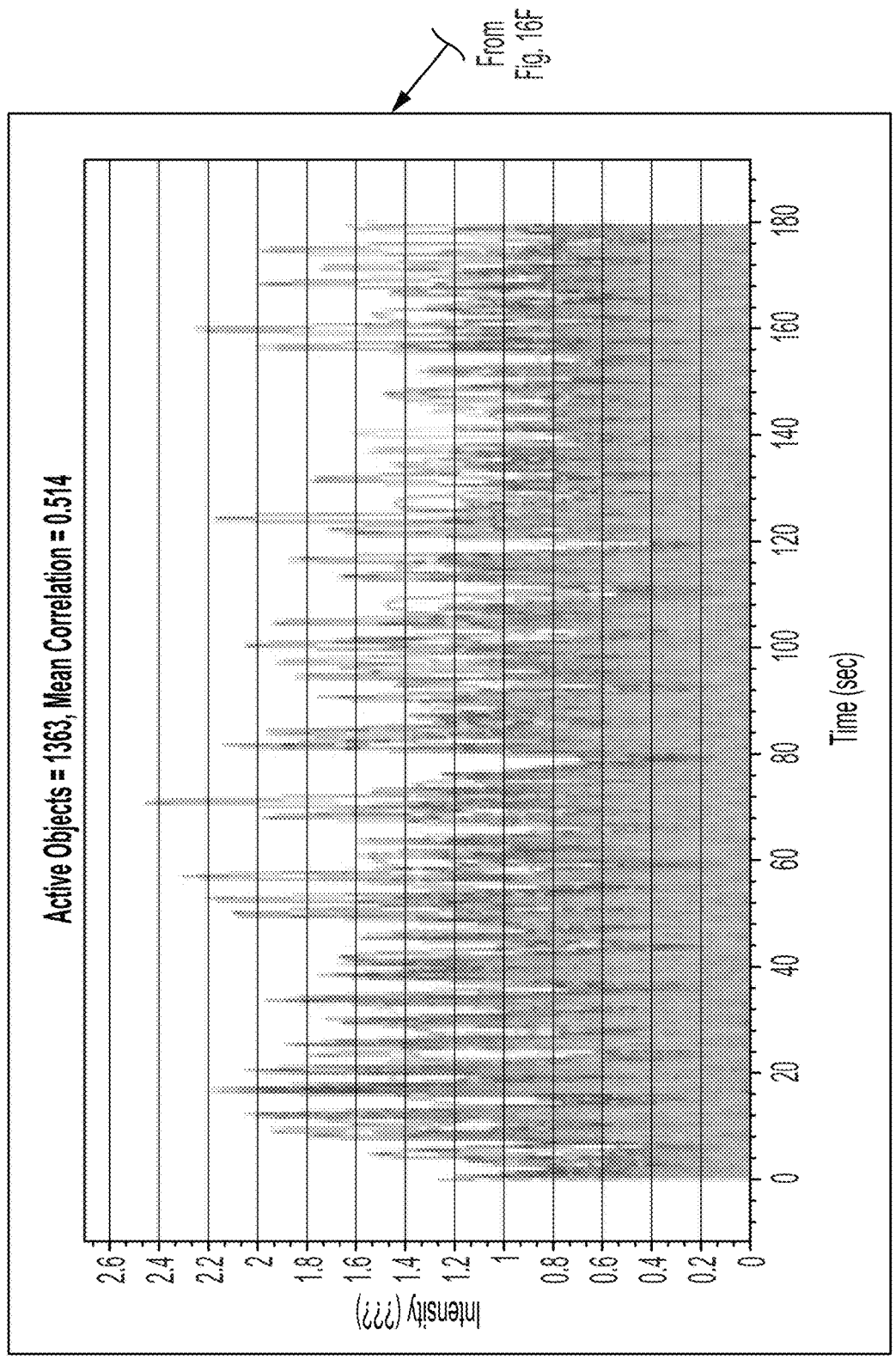
FIG. 16D depicts example experimental results obtained using the systems and methods depicted herein.
Figure 16E:
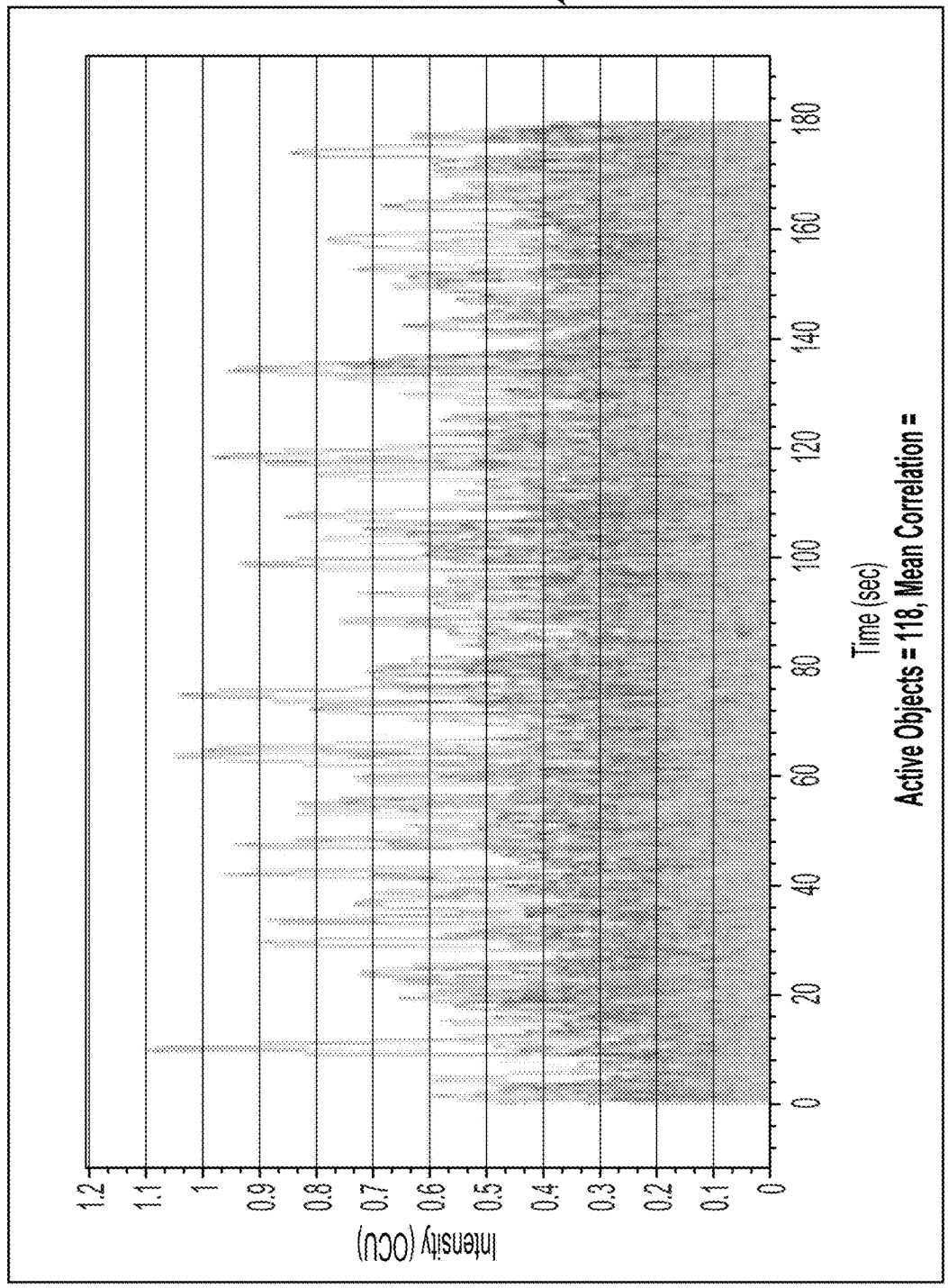
FIG. 16E depicts example experimental results obtained using the systems and methods depicted herein.
Figure 16F:
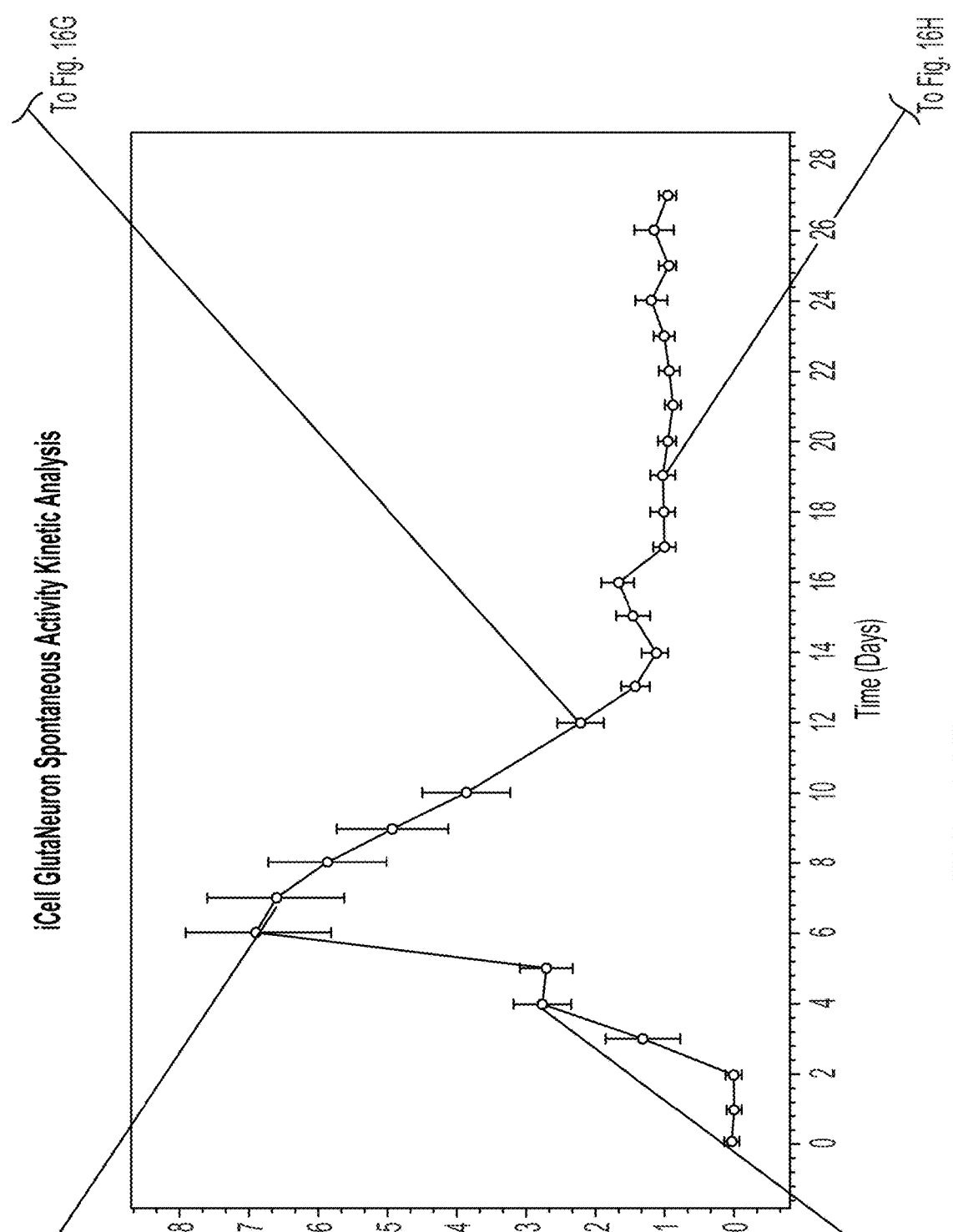
FIG. 16F depicts example experimental results obtained using the systems and methods depicted herein.
Figure 16G:
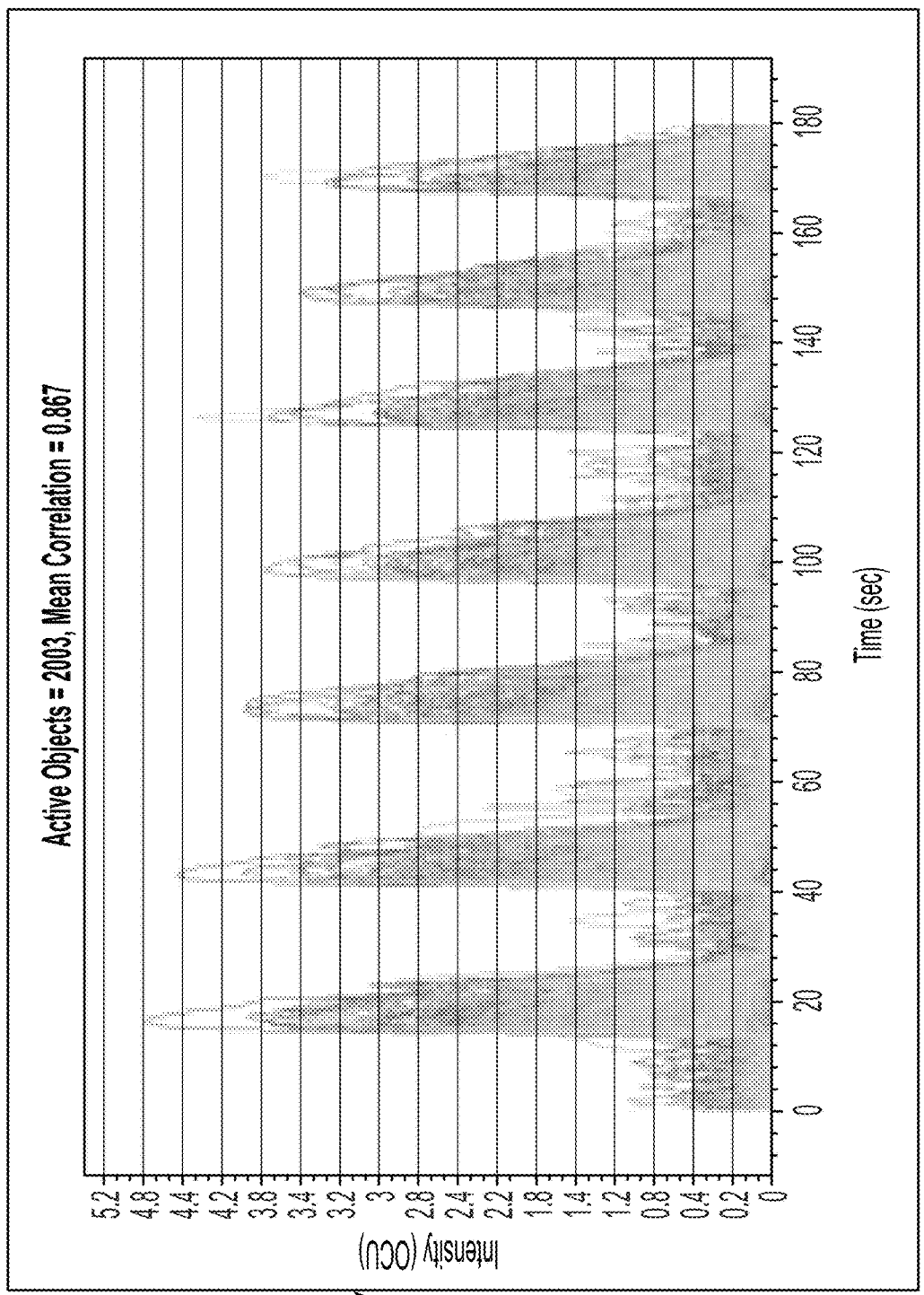
FIG. 16G depicts example experimental results obtained using the systems and methods depicted herein.
Figure 16I:
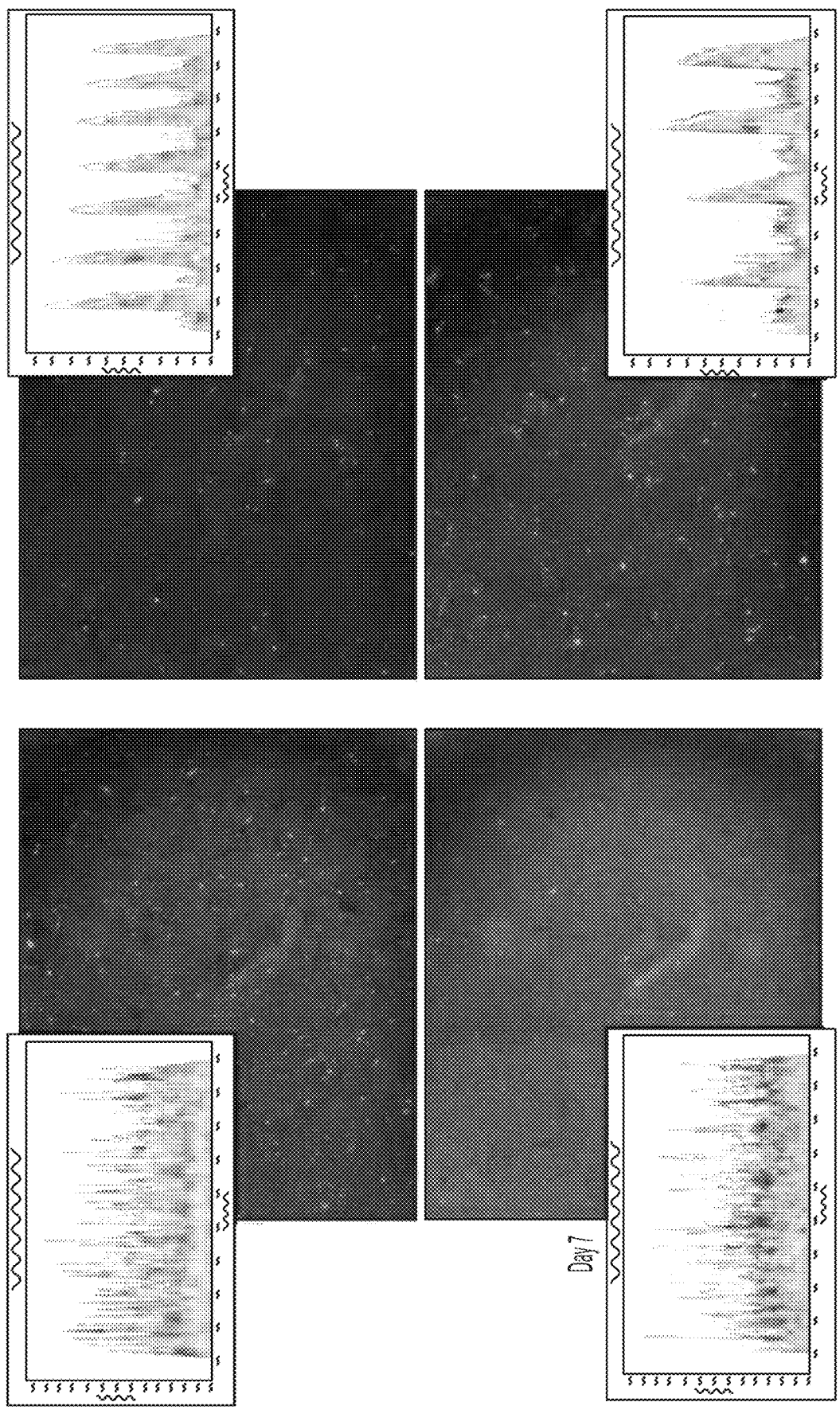
FIG. 16I depicts example experimental results obtained using the systems and methods depicted herein.
Figure 16J:
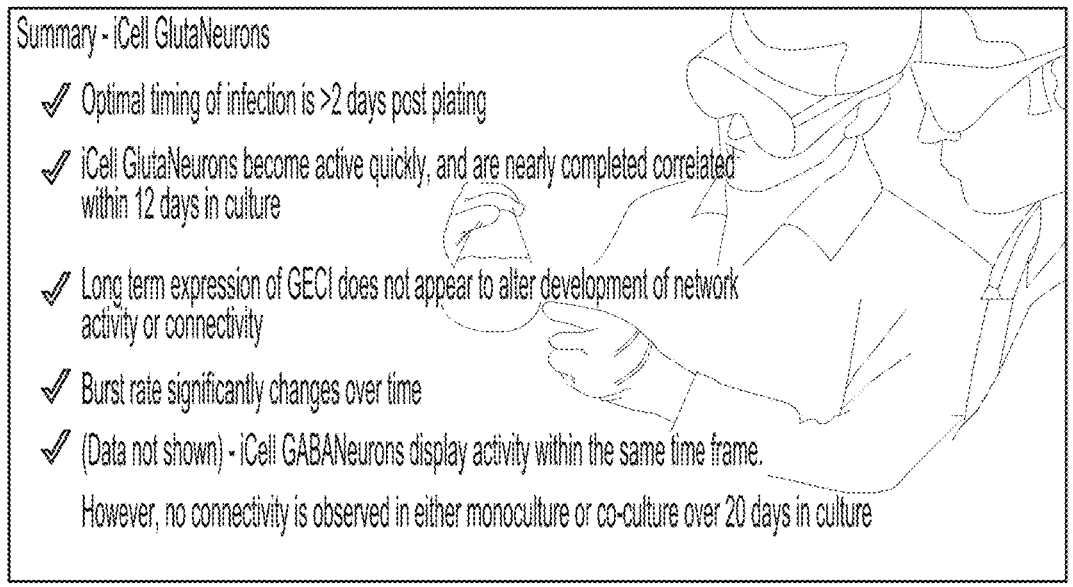
FIG. 16J depicts example experimental results obtained using the systems and methods depicted herein.
Figure 17A:
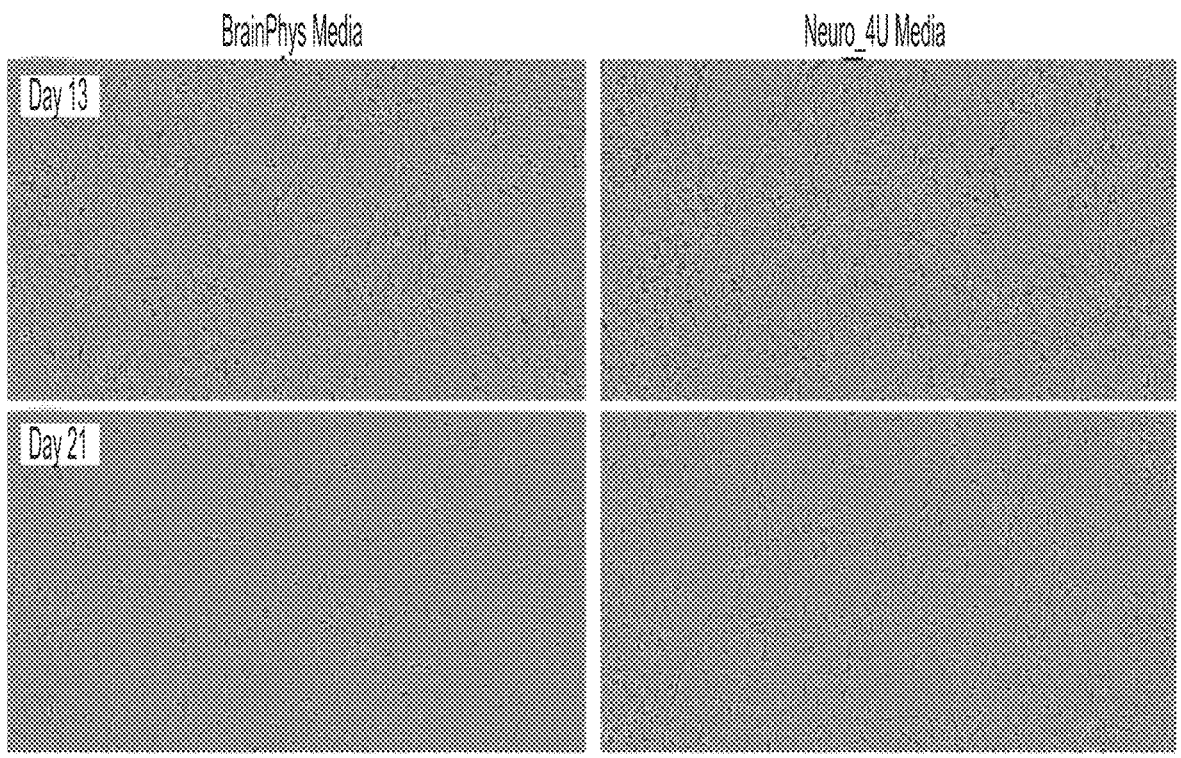
FIG. 17A depicts example experimental results obtained using the systems and methods depicted herein.
Figure 17B:
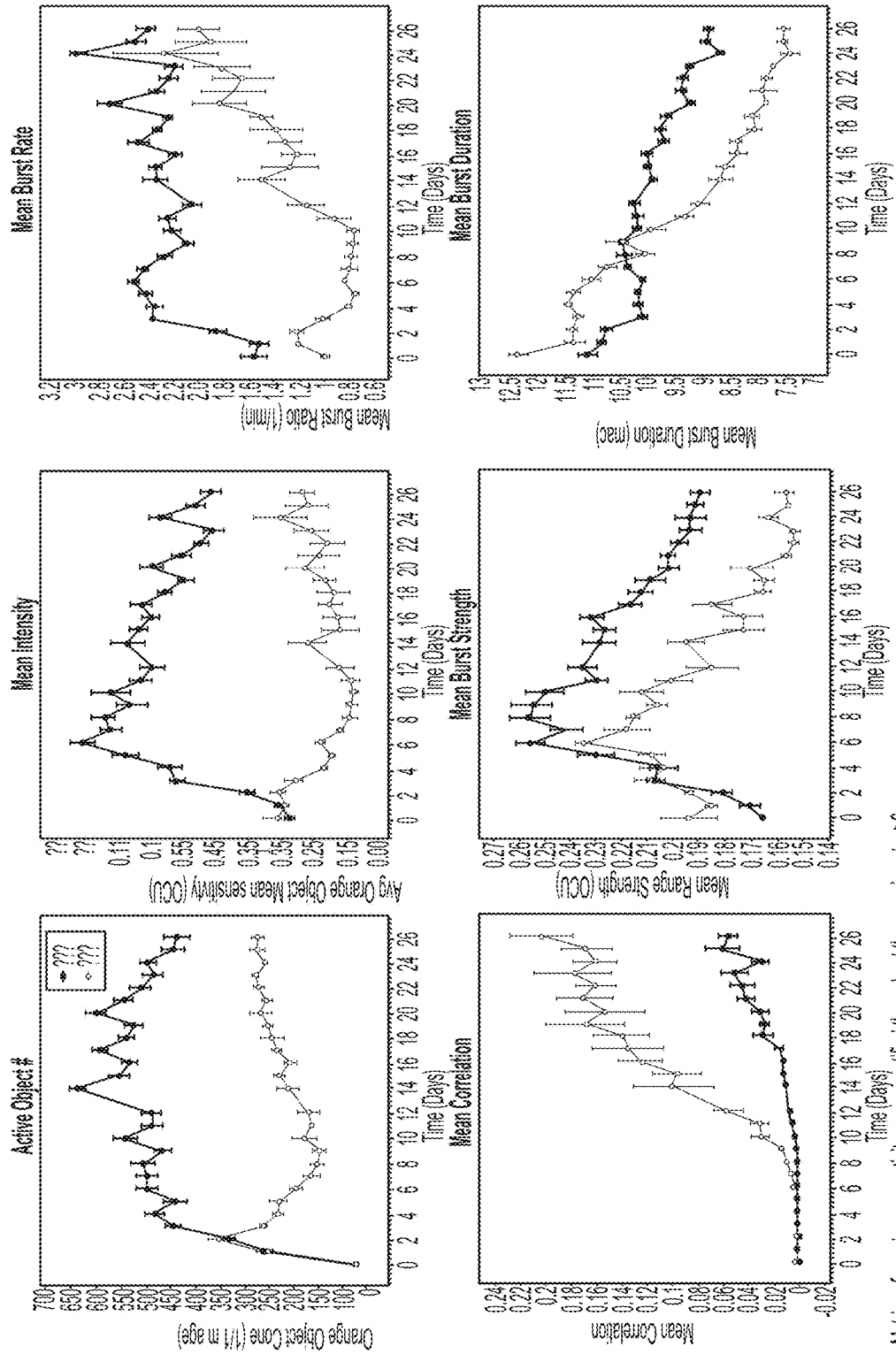
FIG. 17B depicts example experimental results obtained using the systems and methods depicted herein.
Figure 18B:
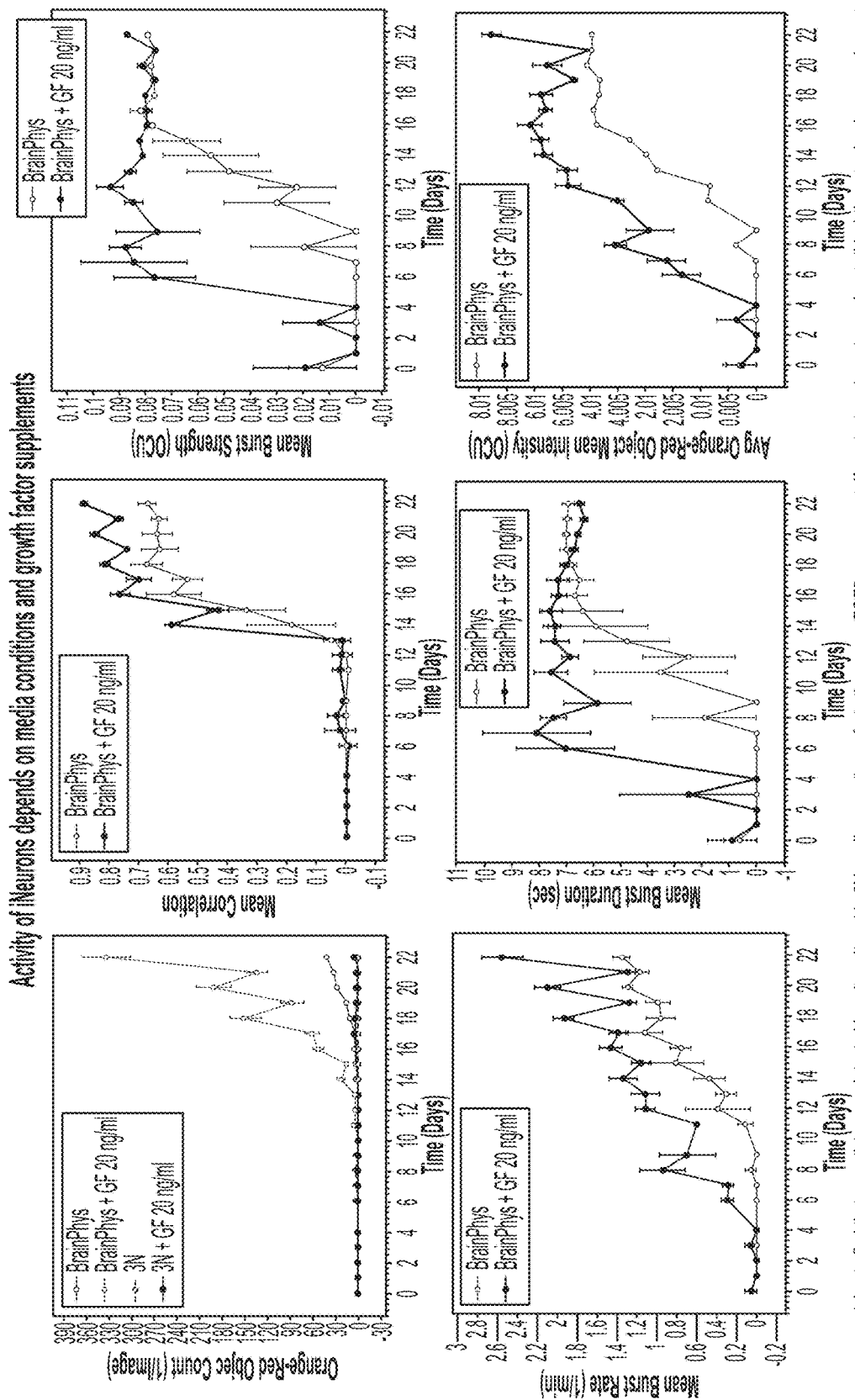
FIG. 18B depicts example experimental results obtained using the systems and methods depicted herein.
Figure 18D:
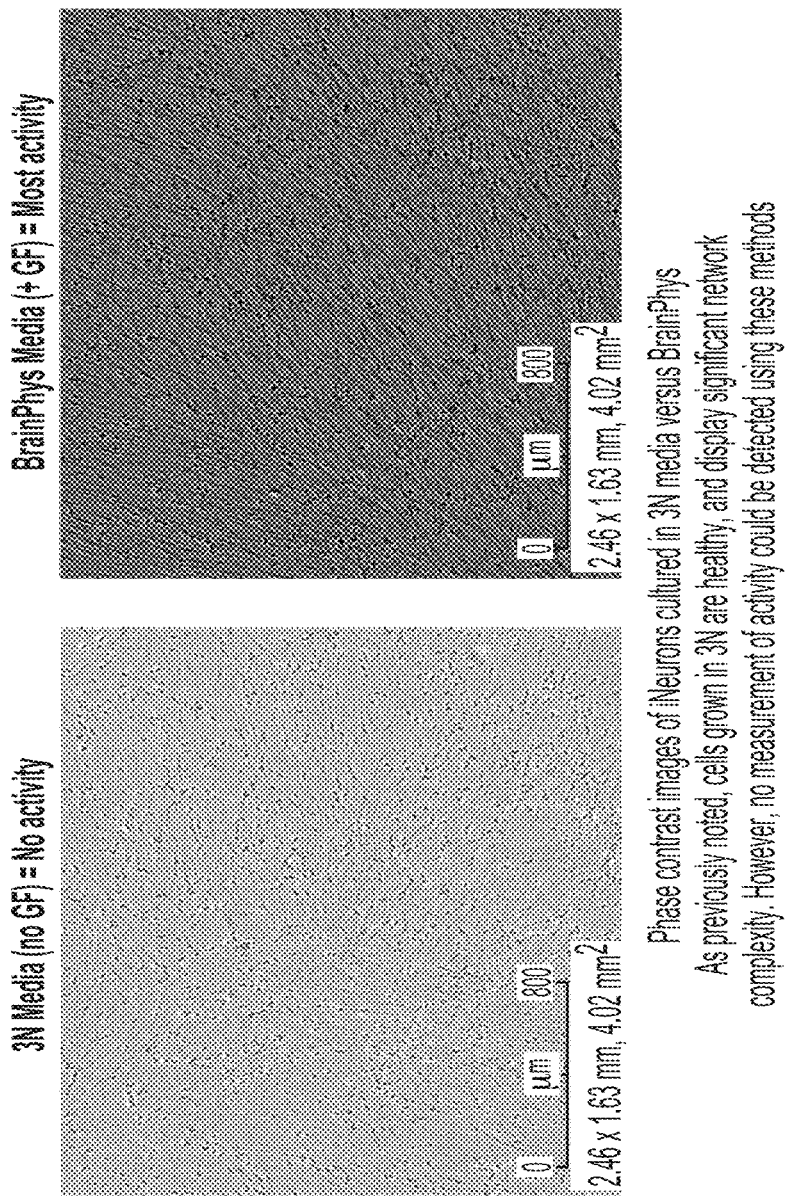
FIG. 18D depicts example experimental results obtained using the systems and methods depicted herein.
Figure 20:
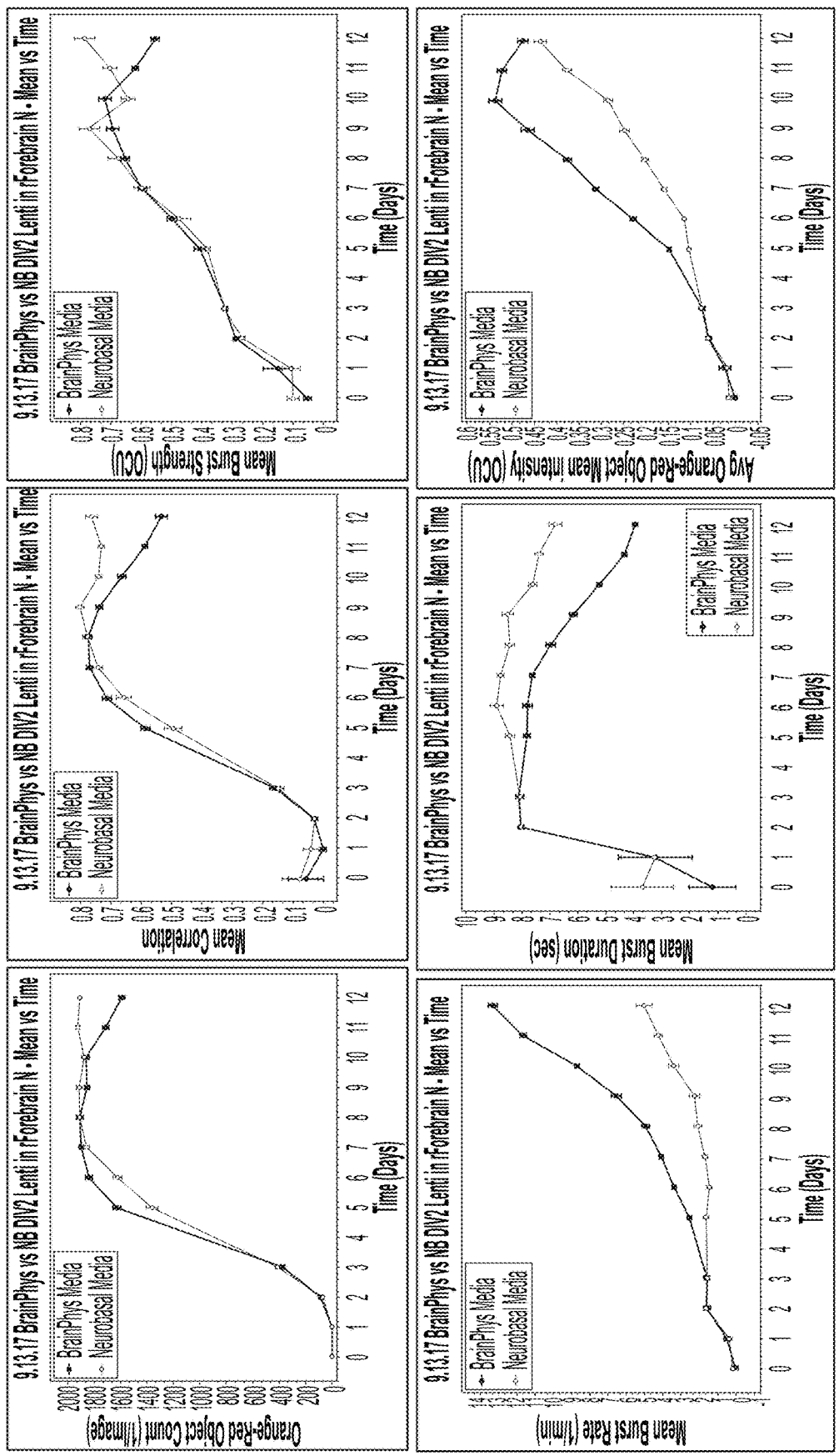
FIG. 20 depicts example experimental results obtained using the systems and methods depicted herein.
Figure 21:
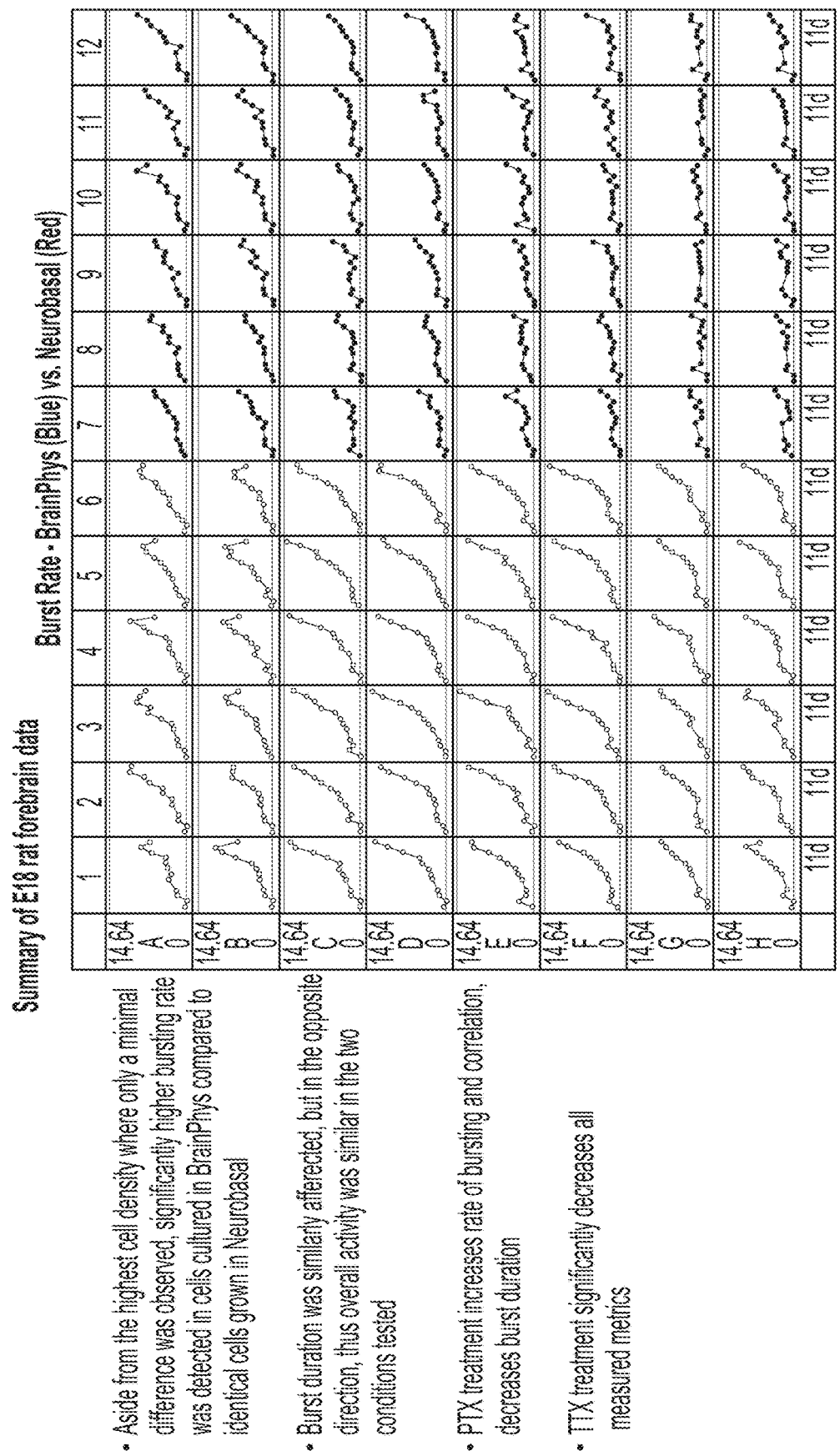
FIG. 21 depicts example experimental results obtained using the systems and methods depicted herein.

FIG. 8 is a flowchart of a method 800 for identifying biologically active cells during one or more periods of time. The method 800 includes, for each of the one or more periods of time, generating a plurality of fluorescence activity images of a sample contained within a sample container (810). The sample includes biologically active cells and each image of the plurality of fluorescence activity images includes a respective plurality of pixel values, each pixel value corresponding to a respective pixel location within an image frame. The method 800 additionally includes, for each of the one or more periods of time, determining a location, relative to the image frame, of one or more active objects within the sample container during a corresponding period of time (820). Each of the one or more active objects is a portion of at least one respective biologically active cell present within the sample during the corresponding period of time.

The method 800 additionally includes, for each of the one or more periods of time and for each of the one or more active objects within the sample container during each corresponding period of time, determining a respective time-varying activity level across the corresponding period of time 830). This can include determining respective time-varying activity levels based on respective sets of pixel values, from each of the plurality of fluorescence activity images, that have pixel locations proximate to the respective determined locations of the one or more active objects. The method 800 additionally includes, for each of the one or more periods of time and based on the time-varying activity levels determined for the one or more active objects, selecting a subset of active objects from the one or more active objects (840). Selecting a particular active object from the one or more active objects includes determining that the time-varying activity level determined for the particular active object exhibits at least one burst.

Either of the methods 700, 800 could include additional elements or features.

V. Example Embodiments

A major impediment to studying human diseases affecting the nervous system is the ability to monitor, analyze, and quantify the activity of neuronal cells that accurately represent human phenotypes.

Currently, various types of cultured neurons are considered promising as models of mammalian neuronal function in both diseased and non-diseased states. However, mammalian neuronal systems are complex and there is a continuing need for tools, including reagents, hardware, software and guided protocols, to characterize cultured neurons, analyze their function, analyze neuronal networks formed by neurons in culture, provide quality controls for cultured neurons and improve induced pluripotent stem cell (iPSC)-derived neuronal cell models.

For example, improved tools for neuronal analysis provided by this disclosure produce better functional cell models to determine parameters such as, but not limited to, whether the cultured neurons are functionally active, when the neurons became functionally active in the cultures and how the functional activity changes over time in culture and under various experimental conditions, what the physical characteristics of the neurons are and how the physical characteristics change over time in culture and under various experimental conditions. Methods and systems provided according to the present disclosure allow a user to make multiple relevant measurements of neuronal cultures which are statistically robust since measurements from thousands of cells are both possible and practical. Methods and systems provided according to the present disclosure allow a user to analyze changes in long-term cultures with higher throughput than previous systems.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Kursad Turksen (Ed.), Embryonic stem cells: methods and protocols in Methods Mol Biol. 2002: 185, Humana Press; Current Protocols in Stem Cell Biology, ISBN: 9780470151808.

The IncuCyte S3 Live Cell Analysis System

The IncuCyte S3 hardware is composed of 2 components: 1) gantry and 2) controller. The gantry houses the microscope, camera, and consumable trays that enable automated image acquisition of live-cell cultures and is installed inside a standard tissue culture incubator. In spontaneous neuronal activity application the microscope system contains a filter module that is tailored to collecting fluorescent images in the orange spectrum (ex: 540 nm; Passband: [513, 568 nm; em: 609 nm; Passband: [577, 684] nm) and in the near-infrared spectrum (ex: 661 nm; Passband: [648, 674]; em: 727 nm; Passband: [641, 771] nm. The controller contains processors, memory and data storage drives that enable image storage, data handling, database storage, file systems, automated image processing, graphing and over-the-network interaction from the client computer through a graphical user interface (GUI). The software on the controller serves 2 purposes: 1) server interaction, and 2) instrument control.

The gantry is installed in an incubator and houses the microscope and camera.

The controller controls the microscope system and functions as a server.

The controller plugs into a communications port, such as, but not limited to, an Ethernet port.

A graphical user interface (GUI) is loaded on to a computer and interacts with the controller (i.e. server) to control the microscope system and interact with the data. All automated image processing is completed on the controller according to aspects of the present disclosure.

Automated Movie Capture

The Incucyte S3 microscope moves to user defined locations of cell culture vessels, such as, but not limited to, 96-well plates, turns on the appropriate LED and captures movies at a desired speed using a desired microscope objective, such as, 3 frames per second (fps) using the 4× objective.

According to particular aspects of the present disclosure, the acquired data is stored in a compressed format, and from that movie a static "Range" image is generated. The range image is composed of pixels representing the minimum fluorescence intensity subtracted from the maximum fluorescence intensity at each pixel location over the complete scan period. Image segmentation is completed on the range image by optimizing multiple parameters, including: background subtraction (top-hat), defining the minimum cell width, fluorescence thresholding. Once objects are defined, an additional user-defined minimum burst intensity filter is used to further define a burst. Each object is typically a neuron, but neuronal parts can also be defined as objects, e.g. dendrites, axons and/or synapses, for example.

From these segmented objects, the following data are derived from the 3 minute scan: 1) correlation—a pairwise correlation analysis of all object traces over the scan period, 2) average object mean intensities—the average of the mean intensities of all objects over the scan period, 3) burst duration—the mean of all objects mean burst duration over the scan period, 5) burst rate—the mean of all objects burst rate over the scan period, 6) burst strength—the strength of each burst is calculated by dividing the area under the intensity curve divided by the duration of the burst. The overall burst strength metric is then the mean of all objects' mean burst strength over the scan period. Lastly the number of active objects is defined by the total number of active objects, i.e. segmented objects within the scan period. Optionally, all seven of these metrics, or a subset thereof, or one or more additional metrics alone or in combination, are calculated for each object, each well, or each set of wells, stored in a database, and displayed to the user shortly following data acquisition in the client computer through the graphical user interface.

Typically wells are scanned every 24 hours, although more or less frequent scanning is an option. Following each scan, metrics are calculated and stored, for instance in the database, at those time points. For example, over the course of a 30 day experiment, 30 time points are collected for each metric, are concatenated into a time series and can be graphed over the course of the full experimental time frame, i.e. hours, days, weeks, months.

As described herein systems and methods of the present disclosure allow users to monitor the changes in neuronal network activity over long periods of time in an automated, moderate throughput way. By contrast, previous methods are: 1) end point methods (can only get one read of the various measured parameters), 2) extremely disruptive methods (calcium dyes versus using genetically encoded calcium indicators, 3) require a user to move cells out of the incubator for analysis/visualization, 4) not statistically relevant (due to making measurements from very few cells), 5) very manual (not automated), or 6) low throughput (one well at a time, manual).

According to aspects of the present disclosure, neurons or neuron-like cells are genetically engineered to express a fluorescent protein, particularly, but not limited to, a calcium indicator protein GCaMP or a variant thereof, such as $Ca^{2+}$ indicator jRCaMP1b and variants thereof, which emits Ca(2+)-dependent fluorescence in the red spectral band.

Embodiments of inventive compositions and methods are illustrated in the following examples. These examples are provided for illustrative purposes and are not considered limitations on the scope of inventive compositions and methods.

IncuCyte S3 Imaging for Spontaneous Neuronal Activity
Experimental Methods: Cells and Reagents The utility of the instrument/system for measuring neuronal activity is exemplified for in long-term imaging experiments with co-cultures of primary and iPSC-derived neurons with rat astrocytes. Temporal changes in intracellular $Ca^{2+}$ is used as a measure of neuronal activity. To make these long-term measurements of intracellular $Ca^{2+}$, neurons were infected with a genetically encoded $Ca^{2+}$ indicator (GECI), jRCaMP1b, via a lentiviral delivery system. jRCaMP1b was licensed from Howard Hughes Medical Institute—US patent: US2016/0176931 A1 and described in Dana et al, eLife 2016:5:e12727. Sample data include experiments from primary rat forebrain neurons as well as three preparations of iPSC-derived neurons: iCell GlutaNeurons (Cellular Dynamics International), Peri.4U neural cells (Ncardia) and iNeurons (University of Michigan).

All experiments were done in 96 well microplates coated with either Poly-D-lysine (rat forebrain neurons), Polyetheneimine/Laminin (iGlutaNeurons and Peri.4U) or Matrigel (iNeurons) to enhance attachment of neurons and astrocytes. All preps were co-cultured with primary rat astrocytes (MTI-Global Stem) at a density of 15,000 cells/well. A mitotic inhibitor (5-Fluoro-2'-deoxyuridine/uridine combination, Sigma Aldrich) was added to reduce proliferation of dividing cells 2 to 3 days post plating. Cultures were maintained for a period of up to 30 days with a 50% change in medium twice per week.

In primary neuronal experiments, rat forebrain neurons (harvested from E-18 embryos (MTI-Global Stem)) were plated at a density range of 5,000 to 40,000 neurons/well in Neurobasal™ Medium (Thermo Fisher) with NeuroCult™ SM1 Neuronal Supplement (Stem Cell Technology) and 2 mM glutamine. One day post plating neurons were infected with the GECI jRCaMP1b. Imaging was initiated 3 days post plating. As an experimental condition, maintenance medium was changed to BrainPhys™ Neuronal Medium (Stem Cell Technology) with NeuroCult™ SM1 Neuronal Supplement (Stem Cell Technologies) in a portion of the plate.

In iCell GlutaNeurons experiments, iCell GlutaNeurons were plated at a density of 30,000 neurons/well in BrainPhys™ Neuronal Medium (Stein Cell Technology) with iCell Neural Supplement B (Cellular Dynamics International), iCell Nervous System Supplement (Cellular Dynamics International) and N2 Supplement (ThermoFisher). One day post plating neurons were infected with the GECI jRCaMP1b. Imaging was initiated 3 days post plating and continued for 27 days.

In Peri.4U neural cell experiments, Peri.4U neural cells were plated at a density of 25,000 neurons/well in Neuro.4U Basal Medium, (Ncardia), and Neuro-Supplement 1 (Ncardia). One day post plating neurons were infected with the GECIjRCaMP1b. Imaging was initiated 3 days post plating. As an experimental condition, maintenance medium was changed to BrainPhys™ Neuronal Medium (Stem Cell Technology) with NeuroCult™ Cm SM1 Neuronal Supplement (Stem Cell Technologies) in a portion of the plate.

In iNeuron experiments, iNeurons were plated at a density of 10,000 neurons/well in 3N media(combination of DMEM/F12 Medium and Neurobasal™ Medium, insulin, Non Essential Amino Acids, ThermoFisher). Twenty one days post plating neurons were infected with the GECI jRCaMP1b. As an experimental condition, maintenance medium was changed to BrainPhys™ Neuronal Medium (Stem Cell Technology) with NeuroCult™ SM1 Neuronal Supplement (Stem Cell Technologies) in a portion of the plate. Imaging was initiated after GECI infection and continued for 10 days.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

VI. Conclusion

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:
1. A method of identifying biologically active cells during one or more periods of time, the method comprising, for each of the one or more periods of time:
  a. generating a plurality of fluorescence activity images of a sample contained within a sample container, wherein the sample includes biologically active cells, and wherein each image of the plurality of fluorescence activity images comprises a respective plurality of pixel values, each pixel value corresponding to a respective pixel location within an image frame;
  b. generating a fluorescence range image from the plurality of fluorescence activity images, wherein generating a fluorescence range image from a plurality of fluorescence activity images comprises determining a plurality of pixel values for the fluorescence range image, and wherein determining a given pixel value for the fluorescence range image comprises determining a range of a set of pixel values, from each of the plurality of fluorescence activity images, that have pixel locations corresponding to a pixel location of the given pixel value within the image frame;

c. based on the fluorescence range image, determining a location, relative to the image frame, of one or more active objects within the sample container during a corresponding period of time, wherein each of the one or more active objects is a portion of at least one respective biologically active cell present within the sample during the corresponding period of time; and d. for each active object of the one or more active objects within the sample container during the corresponding period of time, determining a respective time-varying activity level of each of the one or more active objects across the corresponding period of time.

2. The method of claim 1, wherein the sample container is located within an incubator.

3. The method of claim 1, wherein determining a time-varying activity level of a particular active object during a particular period of time comprises:

determining an uncorrected time-varying activity level based on a set of pixel values, from each of the plurality of fluorescence activity images generated during the particular period of time, that have pixel locations proximate to the determined location of the particular active object;

determining, based on the uncorrected time-varying activity level, a time-varying level of photobleaching of the particular active object across the particular period of time; and determining the time-varying activity level of the particular active object during the particular period of time by removing the time-varying level of photobleaching from the uncorrected time-varying activity level.

4. The method of claim 1, wherein a first period of time of the one or more periods of time and a final period of time of the one or more periods of time are separated in time by more than twenty-four hours.

5. The method of claim 1, wherein the one or more periods of time are regularly spaced over time at a specified rate.

6. The method of claim 5, wherein the specified rate is greater than daily.

7. The method of claim 1, wherein an active object located during a first period of time of the one or more periods of time and an active object located during a different period of time of the one or more periods of time are portions of the same biologically active cell within the sample.

8. The method of claim 1, further comprising:

based on the time-varying activity levels determined for the one or more active objects within the sample container during a particular period of time of the one or more periods of time, determining at least one of a pattern or a degree of coordination between each pair of active objects within the sample container during the particular period of time; and displaying the determined at least one of a pattern or a degree of coordination between each pair of active objects within the sample container during the particular period of time.

9. The method of claim 1, wherein the biologically active cells include at least one of neurons, smooth muscle cells, striated muscle cells, cardiomyocytes, or secretory cells.

10. The method of claim 1, further comprising:

based on the time-varying activity levels determined for the one or more active objects within the sample container during the particular period of time of the one or more periods of time, selecting a subset of active objects, wherein selecting a particular active object from the one or more active objects within the sample container during the particular period of time comprises determining that the time-varying activity level determined for the particular active object exhibits at least one burst.

11. The method of claim 10, further comprising:

based on the time-varying activity levels determined for the selected subset of active objects, determining at least one of a pattern or a degree of coordination between each pair of active objects within the selected subset of active objects; and displaying the determined at least one of a pattern or a degree of coordination between each pair of active objects within the selected subset of active objects.

12. The method of claim 1, wherein determining a location, relative to the image frame, of the one or more active objects within the sample container comprises determining one or more sets of the pixel locations, each set corresponding to an extent within the image frame of a respective active object of the one or more active objects.

13. The method of claim 12, wherein determining a time-varying activity level for a particular active object during a particular period of time of the one or more periods of time comprises determining an aggregate activity level, across the particular period of time, of pixel values that correspond to the determined set of pixel locations that corresponds to the particular active object.

14. The method of claim 1, wherein generating a plurality of fluorescence images for a particular period of time of the one or more periods of time comprises operating a microscope to generate the plurality of fluorescence activity images, and wherein the method further comprises:

prior to generating the plurality of fluorescence images for the particular period of time, operating an actuated gantry to position the microscope relative to the sample container such that the microscope can generate the plurality of fluorescence activity images of the sample for the particular period of time.

15. The method of claim 1, further comprising:

determining a respective degree of photobleaching of the sample represented in each of the fluorescence activity images of a particular plurality of fluorescence activity images that corresponds to a particular period of time of the one or more periods of time; and prior to generating the fluorescence range image for the particular period of time, correcting each of the fluorescence activity images of the particular plurality of fluorescence activity images according to the respective determined degree of photobleaching.

16. The method of claim 1, wherein the biologically active cells include a fluorophore that has a fluorescence property that is related to an activity level of the biologically active cells, and wherein generating a given fluorescence activity image of the sample comprises illuminating the sample at an excitation wavelength of the fluorophore and imaging light that is responsively emitted from the sample at an emission wavelength of the fluorophore.

17. The method of claim 1, further comprising determining, based on respective determined time-varying activity levels, respective mean intensity levels for one or more of the objects during at least one of the one or more periods of time, and/or respective burst rates for one or more of the objects during at least one of the one or more periods of time.

18. A non-transitory computer-readable medium, configured to store at least computer-readable instructions that, when executed by one or more processors of a computing device, cause the computing device to perform computer operations carrying out the method of claim 1.

19. A system comprising:
one or more processors; and
a non-transitory computer-readable medium, configured to store at least computer-readable instructions that, when executed by the one or more processors, cause the system to perform the method of claim 1.

20. A method of identifying biologically active cells during one or more periods of time, the method comprising, for each of the one or more periods of time:
  a. generating a plurality of fluorescence activity images of a sample contained within a sample container, wherein the sample includes biologically active cells, and wherein each image of the plurality of fluorescence activity images comprises a respective plurality of pixel values, each pixel value corresponding to a respective pixel location within an image frame;
  b. generating a fluorescence range image from the plurality of fluorescence activity images, wherein generating a fluorescence range image from a plurality of fluorescence activity images comprises determining a plurality of pixel values for the fluorescence range image, and wherein determining a given pixel value for the fluorescence range image comprises determining a range of a set of pixel values, from each of the plurality of fluorescence activity images, that have pixel locations corresponding to a pixel location of the given pixel value within the image frame;
  c. based on the fluorescence range image, determining a location, relative to the image frame, of one or more active objects within the sample container during a corresponding period of time, wherein each of the one or more active objects is a portion of at least one respective biologically active cell present within the sample during the corresponding period of time; and
  d. for each active object of the one or more active objects within the sample container during the corresponding period of time, determining a respective time-varying activity level of each of the one or more active objects across the corresponding period of time, wherein each time-varying activity level is determined based on a set of pixel values, from each of the plurality of fluorescence activity images, that have pixel locations proximate to the determined location of a corresponding active object.

21. A method of identifying biologically active cells during one or more periods of time, the method comprising, for each of the one or more periods of time:
  a. generating a plurality of fluorescence activity images of a sample contained within a sample container, wherein the sample includes biologically active cells, and wherein each image of the plurality of fluorescence activity images comprises a respective plurality of pixel values, each pixel value corresponding to a respective pixel location within an image frame;
  b. determining a location, relative to the image frame, of one or more active objects within the sample container during a corresponding period of time, wherein each of the one or more active objects is a portion of at least one respective biologically active cell present within the sample during the corresponding period of time;
  c. for each of the one or more active objects within the sample container during the corresponding period of time, determining a respective time-varying activity level across the corresponding period of time; and
  d. based on the time-varying activity levels determined for the one or more active objects, selecting a subset of active objects from the one or more active objects, wherein selecting a particular active object from the one or more active objects comprises determining that the time-varying activity level determined for the particular active object exhibits at least one burst; or
  (i) generating a plurality of fluorescence activity images of a sample contained within a sample container, wherein the sample includes biologically active cells, and wherein each image of the plurality of fluorescence activity images comprises a respective plurality of pixel values, each pixel value corresponding to a respective pixel location within an image frame;
  (ii) determining a location, relative to the image frame, of one or more active objects within the sample container during a corresponding period of time, wherein each of the one or more active objects is a portion of at least one respective biologically active cell present within the sample during the corresponding period of time;
  (iii) for each of the one or more active objects within the sample container during the corresponding period of time, determining a respective time-varying activity level across the corresponding period of time based on respective sets of pixel values, from each of the plurality of fluorescence activity images, that have pixel locations proximate to the respective determined locations of the one or more active objects; and
  (iv) based on the time-varying activity levels determined for the one or more active objects, selecting a subset of active objects from the one or more active objects, wherein selecting a particular active object from the one or more active objects comprises determining that the time-varying activity level determined for the particular active object exhibits at least one burst.

* * * * *